United States Patent
Katsuraku et al.

(10) Patent No.: US 10,090,124 B2
(45) Date of Patent: Oct. 2, 2018

(54) ROTARY SWITCHING DEVICE SELECTION ELEMENT INFORMATION DISPLAY

(71) Applicant: Sony Corporation, Tokyo (JP)

(72) Inventors: Junko Katsuraku, Tokyo (JP); Koya Nomoto, Aichi (JP); Shuji Fujita, Tokyo (JP); Tsunetoshi Samukawa, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 15/542,555

(22) PCT Filed: Sep. 23, 2016

(86) PCT No.: PCT/JP2016/078110
§ 371 (c)(1),
(2) Date: Jul. 10, 2017

(87) PCT Pub. No.: WO2017/086023
PCT Pub. Date: May 26, 2017

(65) Prior Publication Data
US 2018/0025864 A1   Jan. 25, 2018

(30) Foreign Application Priority Data

Nov. 18, 2015 (JP) .................. 2015-225537
Jul. 21, 2016 (JP) .................. 2016-143636

(51) Int. Cl.
*G04B 19/04* (2006.01)
*G09F 13/04* (2006.01)
(Continued)

(52) U.S. Cl.
CPC ............. *H01H 19/14* (2013.01); *G04B 19/04* (2013.01); *G09F 2013/0422* (2013.01); *G09F 2013/145* (2013.01); *H01H 19/025* (2013.01)

(58) Field of Classification Search
CPC .... H04N 13/042; H04N 13/042; G02B 23/10; G09F 2013/0422; G09F 2013/0477; G09F 2013/145; G04B 19/01; G04B 19/34
(Continued)

(56) References Cited

U.S. PATENT DOCUMENTS 3,650,599 A * 3/1972 Pedersen ................ G04B 19/34
116/304
5,311,687 A * 5/1994 Reed ....................... G09F 13/04
362/324
(Continued)

FOREIGN PATENT DOCUMENTS

DE        7309838 U     2/1973
JP     33-014147 Y1    9/1958
(Continued)

OTHER PUBLICATIONS

Extended European Search Report dated Jul. 12, 2018 in connection with European Application No. 16866026.4.

*Primary Examiner* — Vanessa Girardi
(74) *Attorney, Agent, or Firm* — Wolf, Greenfield & Sacks, P.C.

(57) ABSTRACT

[Object] To enable to visually recognizing information displayed on an outer circumferential surface of a member from an axial direction of the member and capable of switching selection elements while viewing the device from the axial direction.
[Solution] A rotary switching device includes: a cylindrical first member that includes an outer circumferential surface on which predetermined information is displayed; a second member that is rotatable relative to the first member; a plurality of selection elements among which a selection target is switched in accordance with relative positions of the first member and the second member; a mirror surface part that is formed by a surface disposed around the outer
(Continued)

circumferential surface of the first member and intersecting an axial direction of the first member, and that is configured to specularly reflect the information displayed on the outer circumferential surface of the first member to enable the information to be visually recognized from the axial direction of the first member; and an indicating part configured to indicate the selection element that is selected.

13 Claims, 27 Drawing Sheets

(51) Int. Cl.
*H01H 19/14* (2006.01)
*H01H 19/02* (2006.01)
*G09F 13/14* (2006.01)

(58) Field of Classification Search
USPC .......................................... 359/439; 353/81
See application file for complete search history.

(56) References Cited

U.S. PATENT DOCUMENTS

| | | | |
|---|---|---|---|
| 6,050,697 A * | 4/2000 | Bennington | A23G 3/50 362/109 |
| 7,520,615 B2 * | 4/2009 | Hoshino | G03B 21/14 345/653 |
| 7,559,243 B1 * | 7/2009 | Hawkins | G01D 5/145 324/696 |
| 8,024,879 B2 * | 9/2011 | Pulfer | G09F 13/02 215/6 |
| 9,470,392 B2 * | 10/2016 | Santiago | F21S 4/10 |
| 2009/0072046 A1 | 3/2009 | Feuillard et al. | |

FOREIGN PATENT DOCUMENTS

| | | |
|---|---|---|
| JP | 63-024593 A | 2/1988 |
| JP | 07-232687 A | 9/1995 |
| JP | 09-002210 A | 1/1997 |
| JP | 2004-208896 A | 7/2004 |

\* cited by examiner

ROTARY SWITCHING DEVICE SELECTION ELEMENT INFORMATION DISPLAY

TECHNICAL FIELD

The present disclosure relates to a rotary switching device.

BACKGROUND ART

Conventionally, a rotary switching device that enables a selection of a desired selection element from a plurality of selection elements by a rotation operation is used in various fields. Examples of the rotary switching device include a rotating switch for switching an interval at an intermittent operation of a wiper of a vehicle and a rotating operating device provided at a handle part for switching a gear shift stage of a bicycle (For example, refer to Patent Literatures 1 and 2).

In the conventional rotary switching devices exemplified in Patent Literatures 1 and 2, an operator performs a switching operation while viewing the device from a circumferential surface side of a rotating operating part. In such a rotary switching device, because selection elements that can be selected are displayed on the circumferential surface of the device, the operator can operate the device while recognizing a position to which the operator should rotate the device to select a desired selection element desired. Also, in the rotary switching devices described in Patent Literatures 1 and 2, selection elements are regularly arranged. Therefore, the operator can select a desired selection element by sequentially performing a rotation operation in a certain direction until a desired selection state is reached.

CITATION LIST

Patent Literature

Patent Literature 1: JP H09-2210A
Patent Literature 2: JP H07-232687A

DISCLOSURE OF INVENTION

Technical Problem

However, in the case of operating the rotary switching devices disclosed in Patent Literatures 1 and 2 while viewing the device from an axial direction of the rotating operating part, it may be impossible to operate the device while recognizing selection elements that can be selected. Particularly, when the selection elements are arranged irregularly or can be switched to other selection elements, the operator can no longer recognize which selection element can be selected at which position.

Therefore, according to the present disclosure, there is provided a novel and improved rotary switching device that enables an operator to visually recognizing information displayed on an outer circumferential surface of a member from an axial direction of the member and capable of switching selection elements while viewing the device from the axial direction.

Solution to Problem

According to the present disclosure, there is provided a rotary switching device including: a cylindrical first member that includes an outer circumferential surface on which predetermined information is displayed; a second member that is rotatable relative to the first member; a plurality of selection elements among which a selection target is switched in accordance with relative positions of the first member and the second member; a mirror surface part that is formed by a surface disposed around the outer circumferential surface of the first member and intersecting an axial direction of the first member, and that is configured to specularly reflect the information displayed on the outer circumferential surface of the first member to enable the information to be visually recognized from the axial direction of the first member; and an indicating part configured to indicate the selection element that is selected.

Advantageous Effects of Invention

As described above, according to the present disclosure, information displayed on an outer circumferential surface of a member can be visually recognized from an axial direction of the member and selection elements may be switched while viewing the device from the axial direction. Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
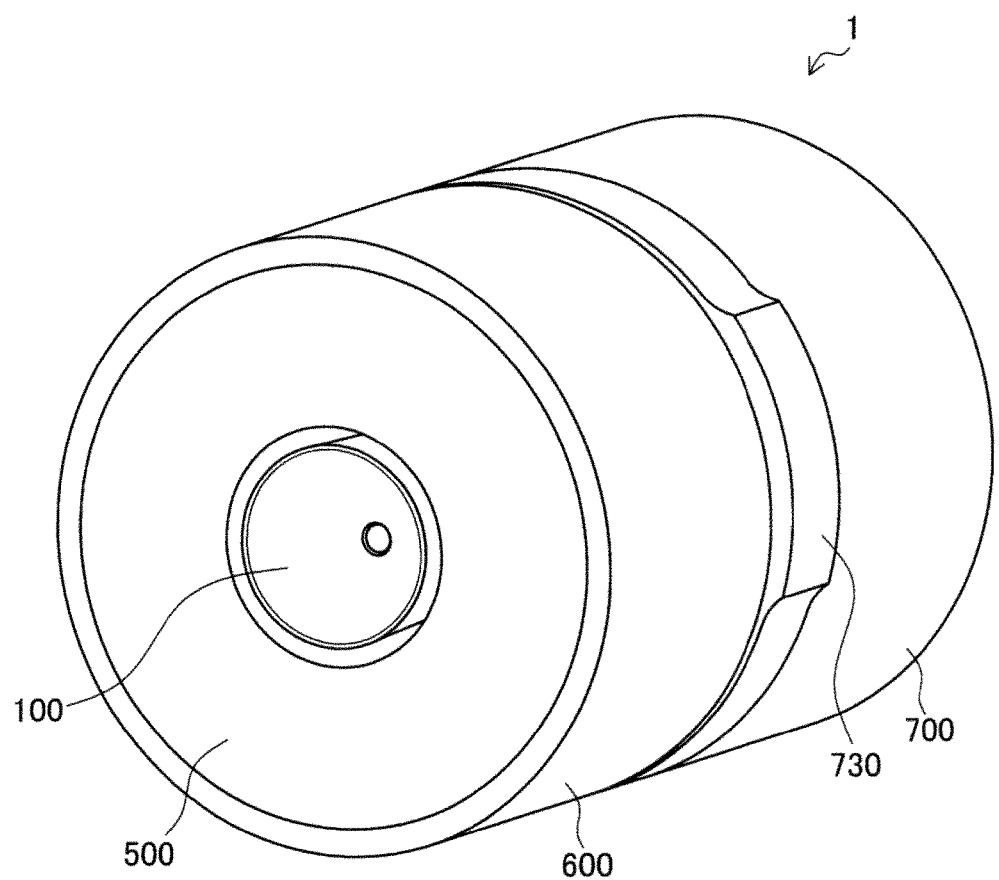
FIG. 1 is a perspective view illustrating an aromatic device which is a rotary switching device according to a first embodiment of the present disclosure.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

The description will be given in the following order.
1. First embodiment
1.1. Configuration example of rotary switching device
1.2. Summary
2. Second embodiment
3. Third embodiment 1. First Embodiment <1-1. Configuration Example of Rotary Switching Device>
(1-1-1. Overall Configuration)

Figure 2:
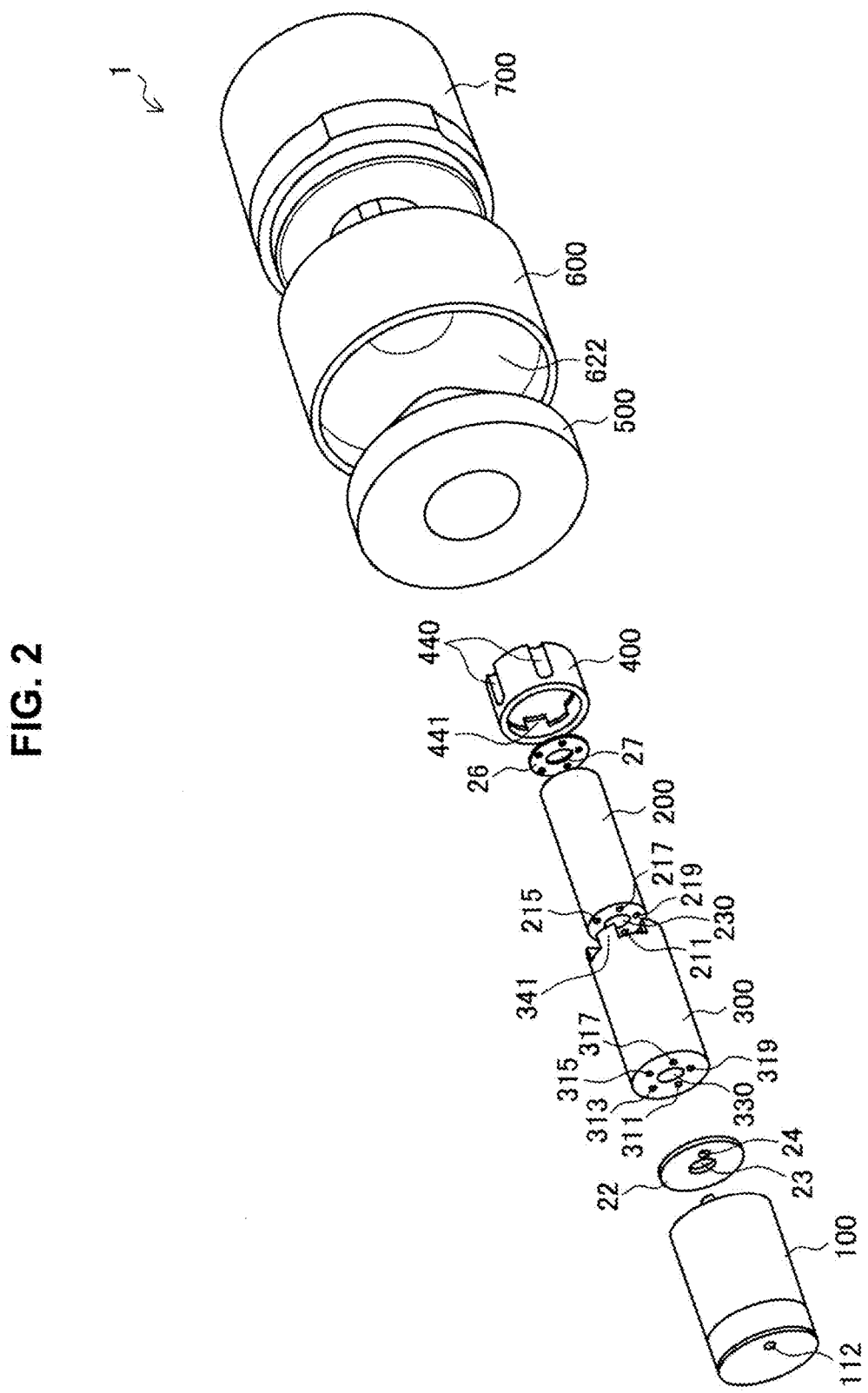
FIG. 2 is an exploded perspective view of the aromatic device according to the same embodiment.
Figure 3:
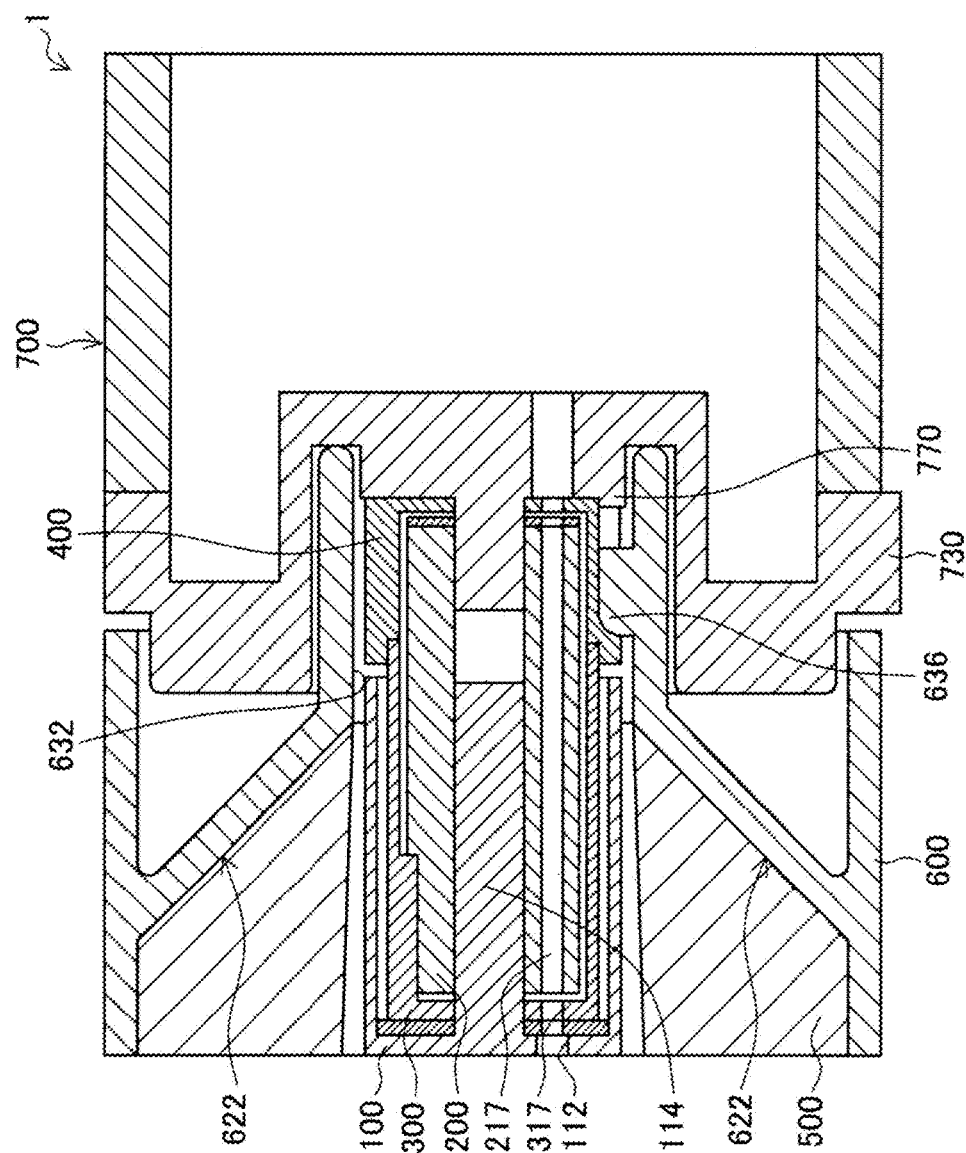
FIG. 3 is an axial cross-sectional view illustrating a portion of the aromatic device according to the same embodiment.
Figure 4:
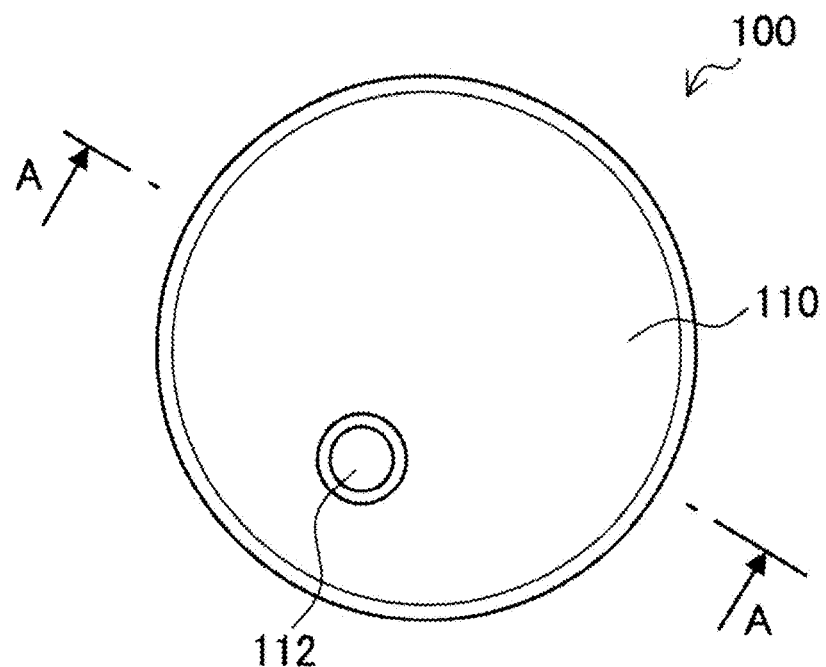
FIG. 4 is a view of a third member of the aromatic device according to the same embodiment when seen from the axial direction.
Figure 5:
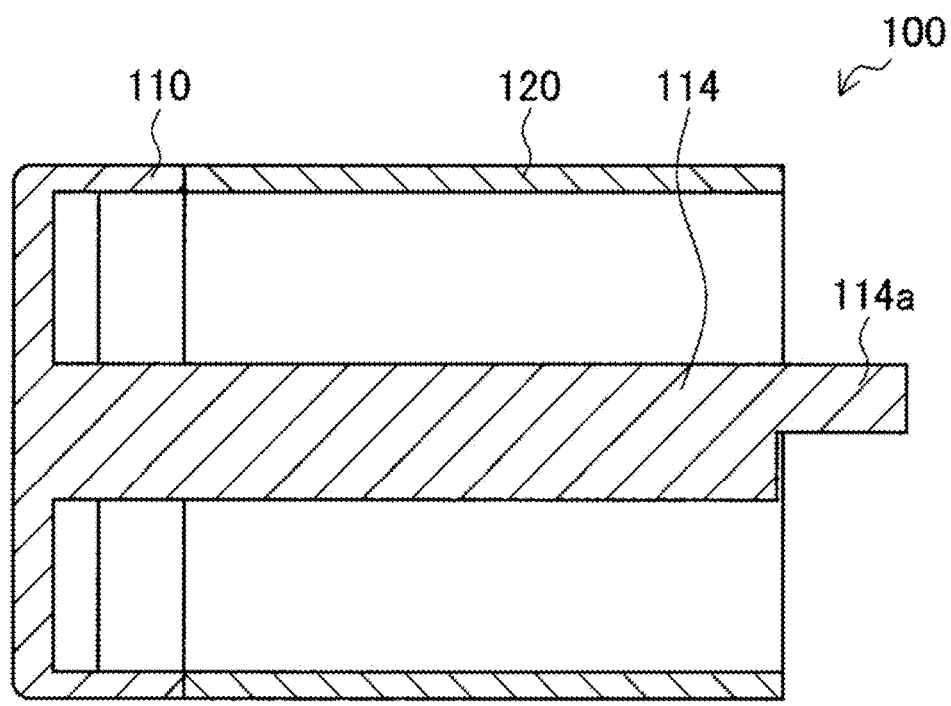
FIG. 5 is an axial cross-sectional view of the third member of the aromatic device according to the same embodiment.
Figure 6:
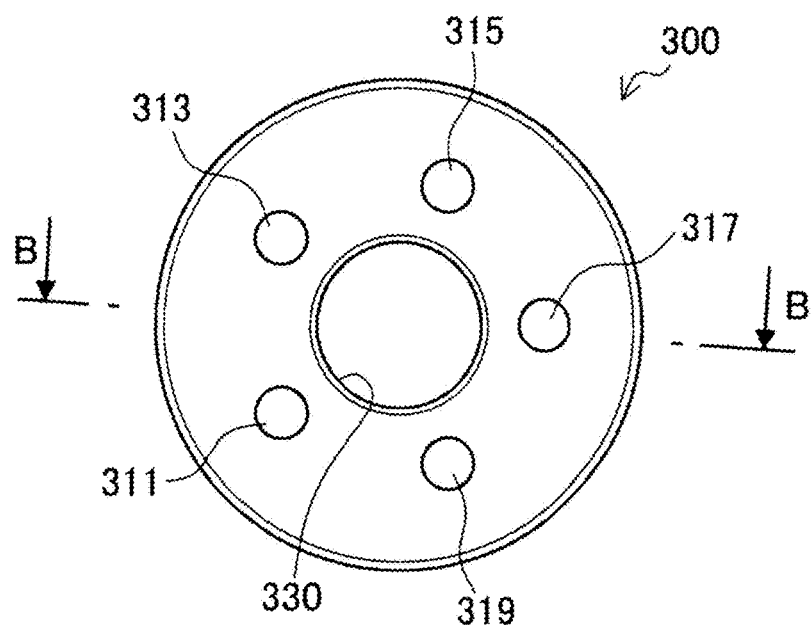
FIG. 6 is a view of a first member of the aromatic device according to the same embodiment when seen from the axial direction.
Figure 7:
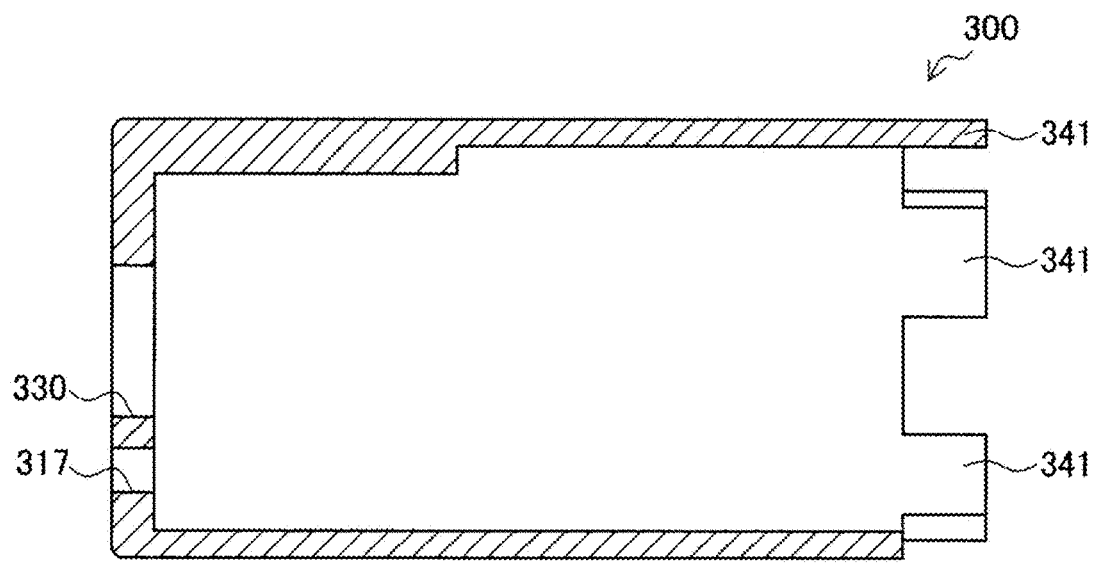
FIG. 7 is an axial cross-sectional view of the first member of the aromatic device according to the same embodiment.
Figure 8:
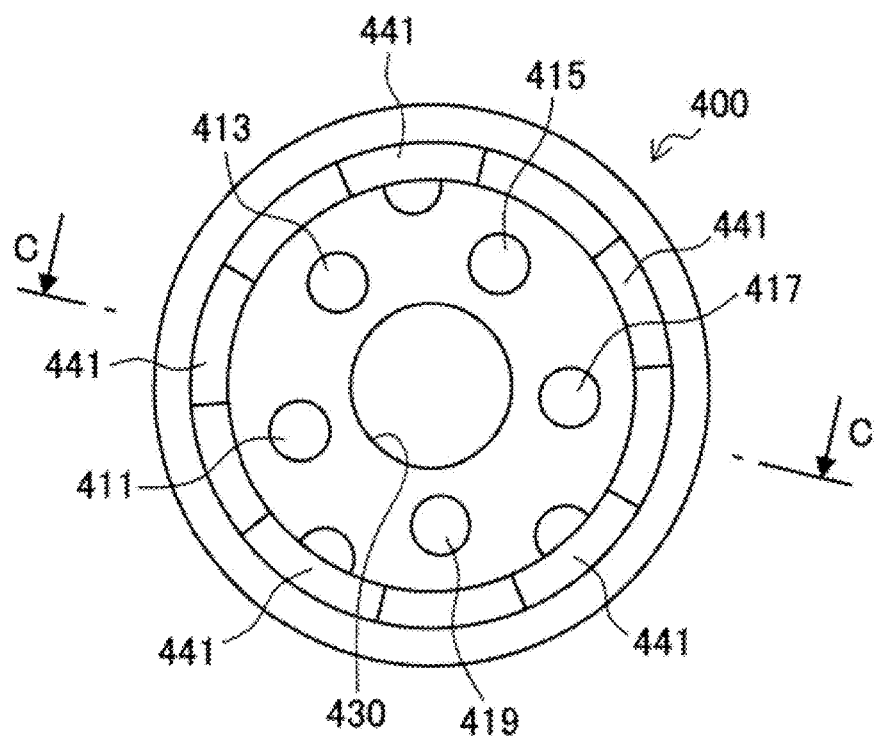
FIG. 8 is a view of a holding part of the aromatic device according to the same embodiment when seen from the axial direction.
Figure 9:
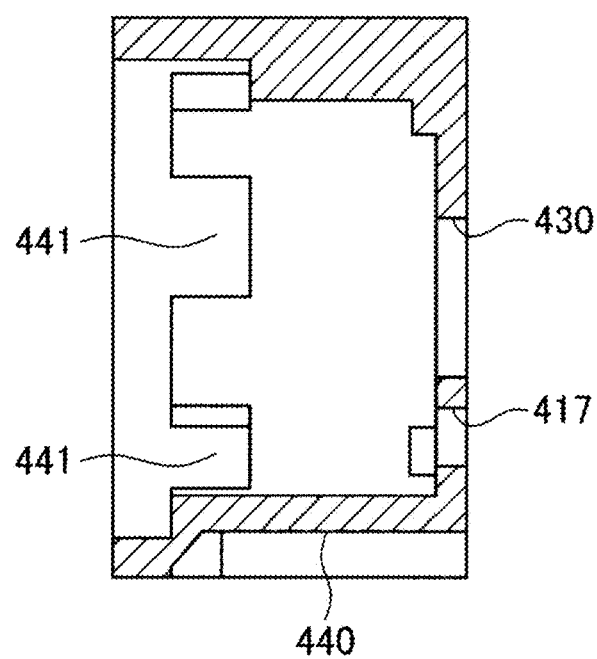
FIG. 9 is an axial cross-sectional view of the holding part of the aromatic device according to the same embodiment.
Figure 10:
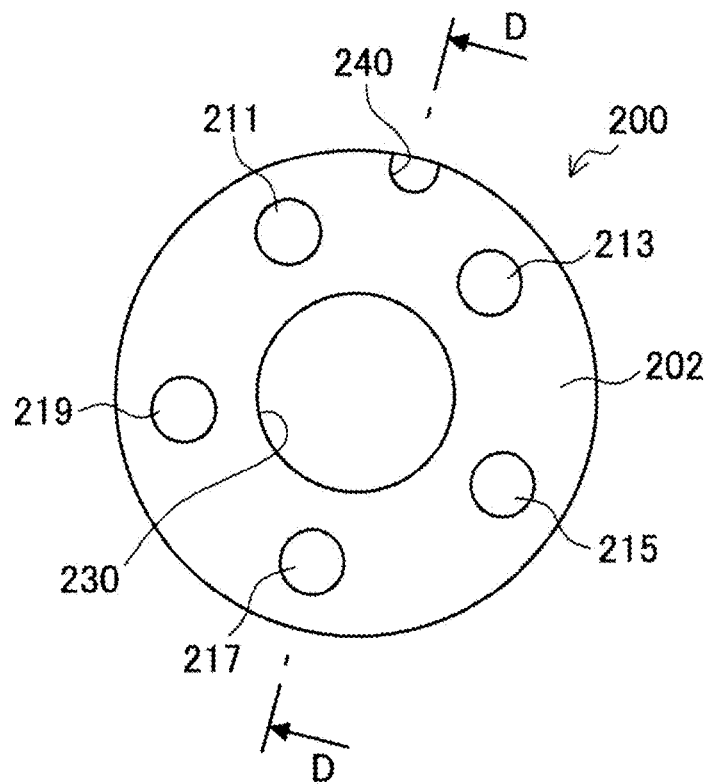
FIG. 10 is a view of a perfume cartridge of the aromatic device according to the same embodiment when seen from the axial direction.
Figure 11:
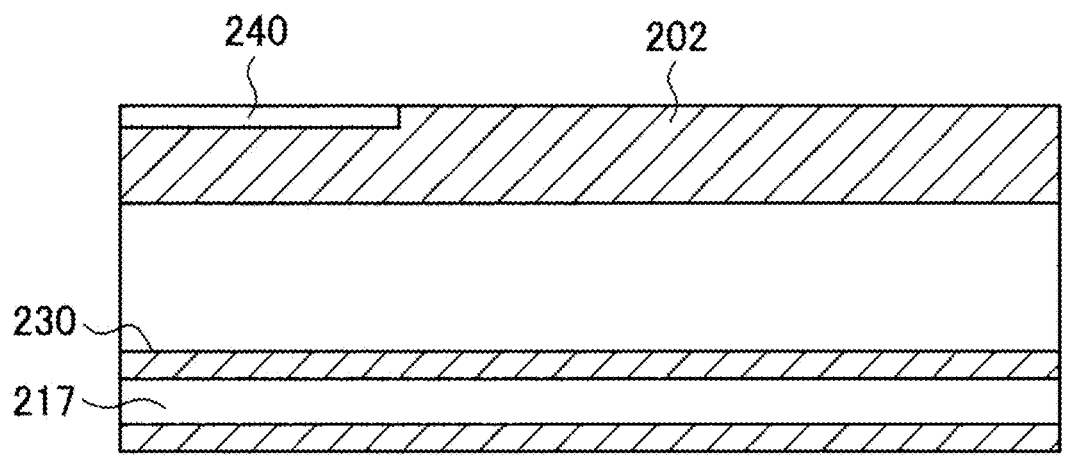
FIG. 11 is an axial cross-sectional view of the perfume cartridge of the aromatic device according to the same embodiment.
Figure 12:
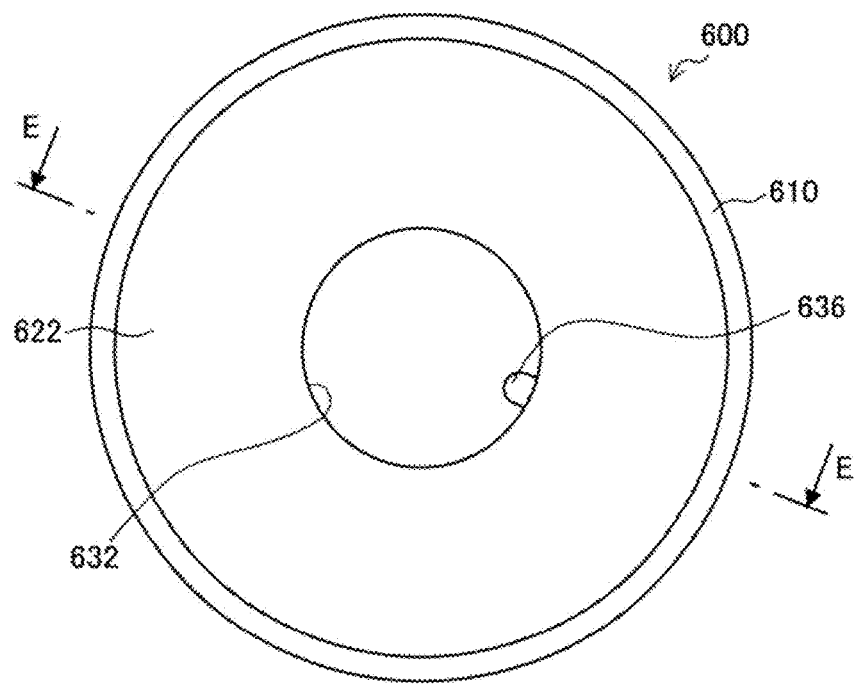
FIG. 12 is a view of a rotating operating part of the aromatic device according to the same embodiment when seen from the axial direction.
Figure 13:
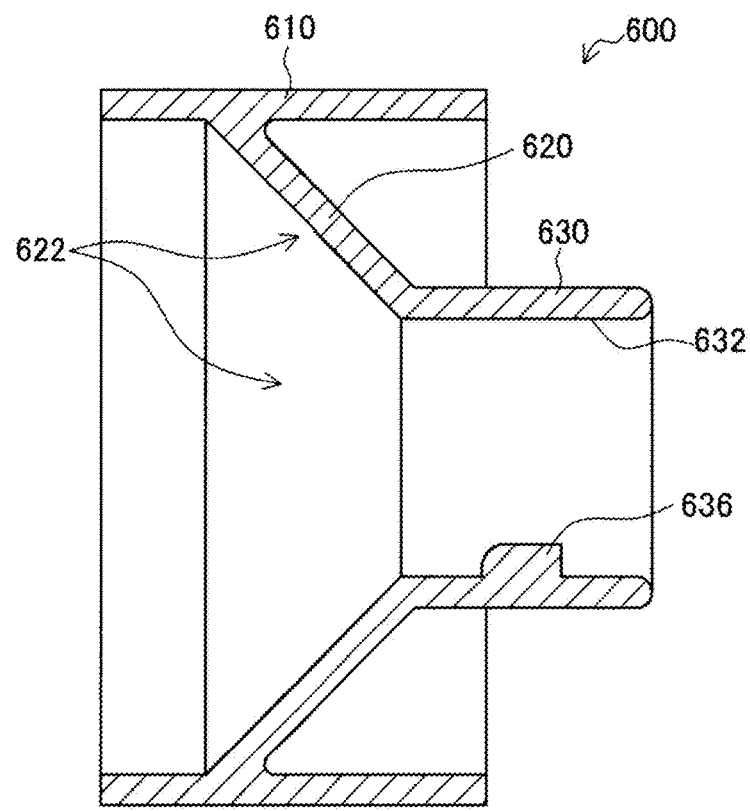
FIG. 13 is an axial cross-sectional view of the rotating operating part of the aromatic device according to the same embodiment.
Figure 14:
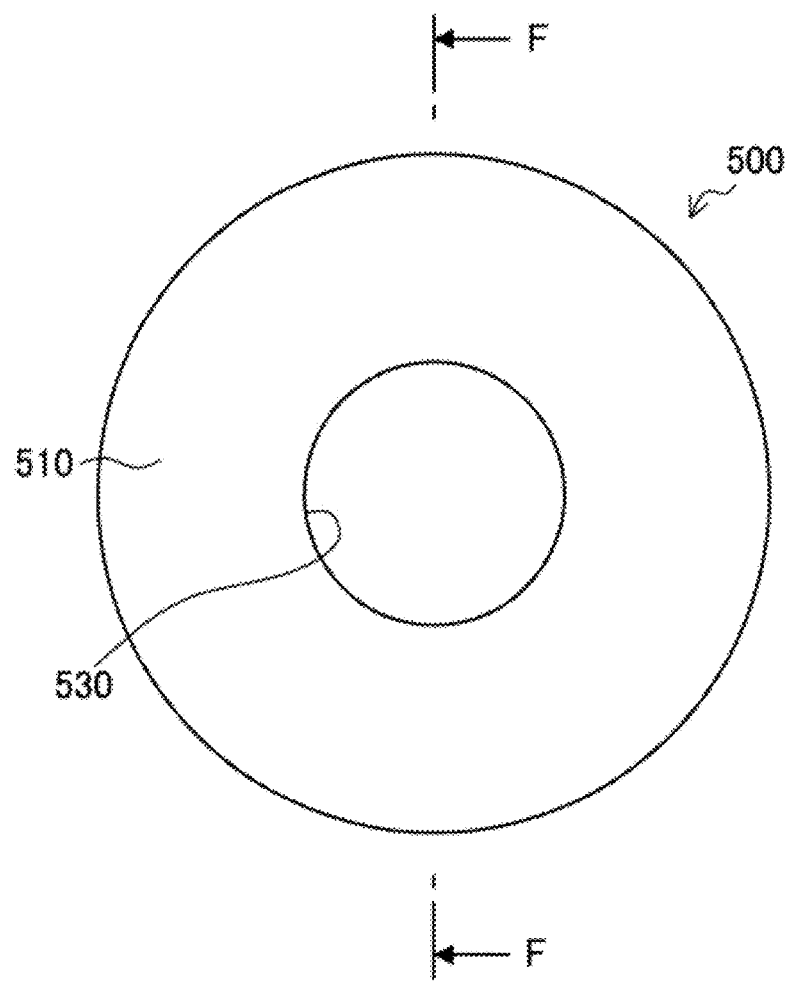
FIG. 14 is a view of a prism part of the aromatic device according to the same embodiment when seen from the axial direction.
Figure 15:
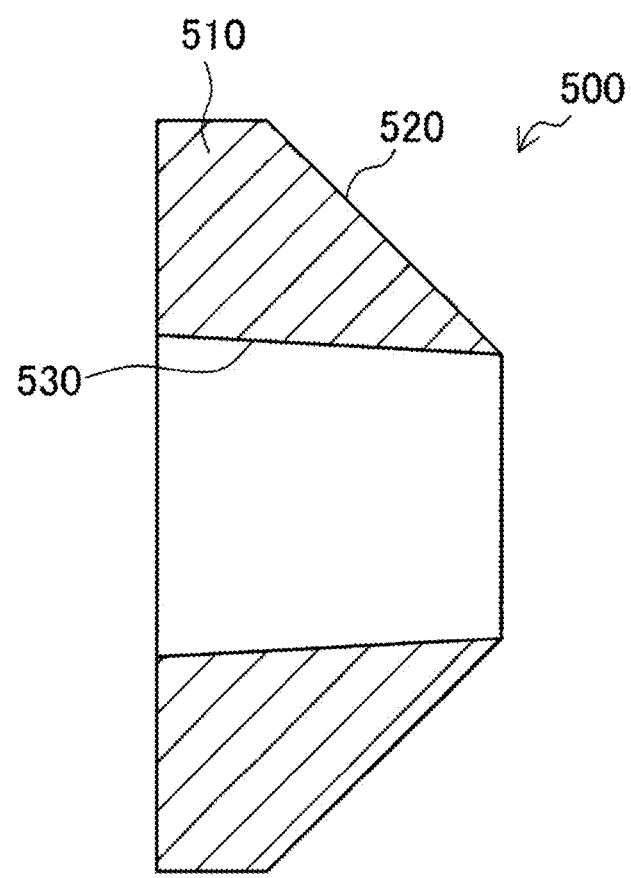
FIG. 15 is an axial cross-sectional view of the prism part of the aromatic device according to the same embodiment.
Figure 16:
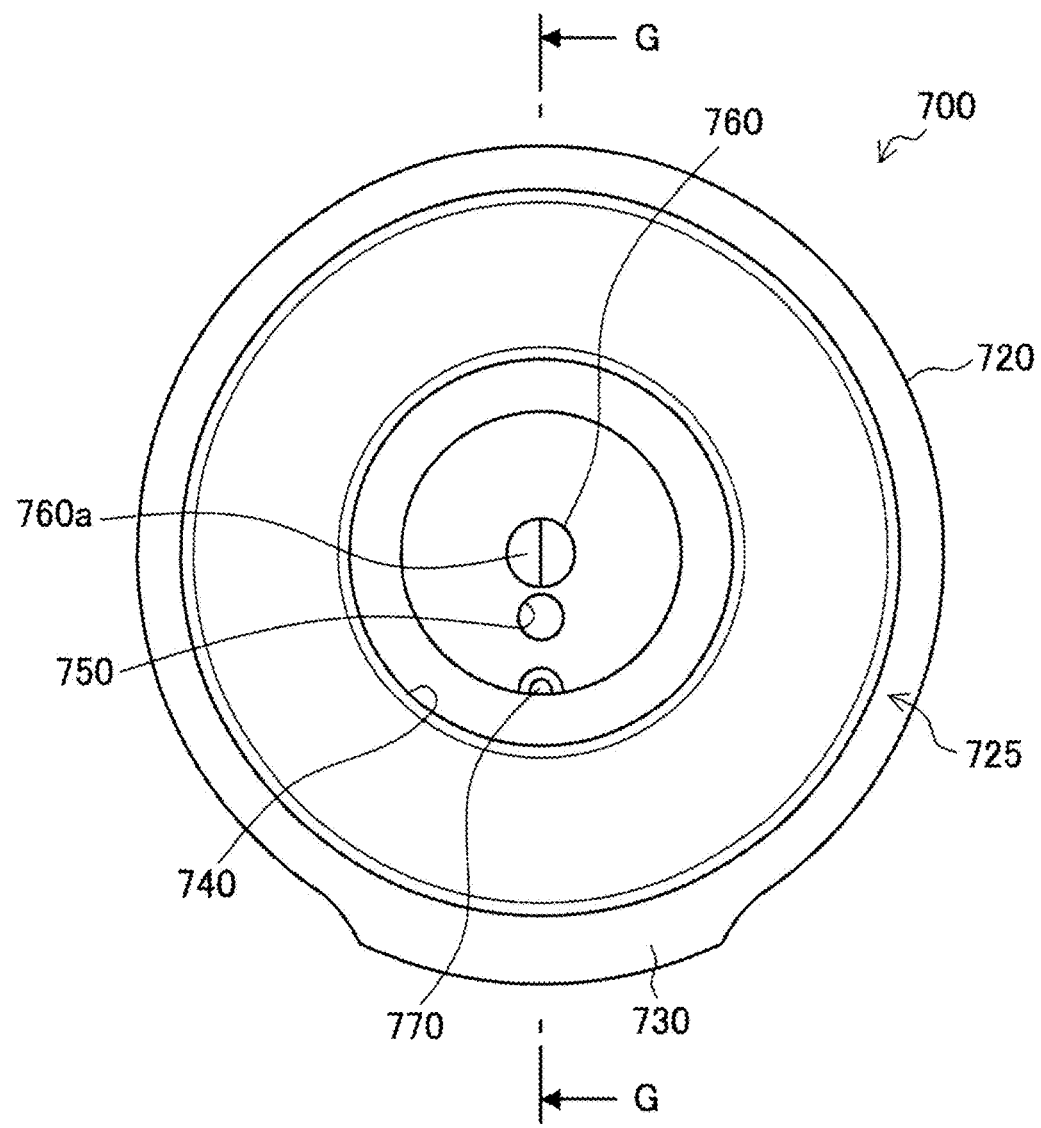
FIG. 16 is a view of a second member of the aromatic device according to the same embodiment when seen from the axial direction.
Figure 17:
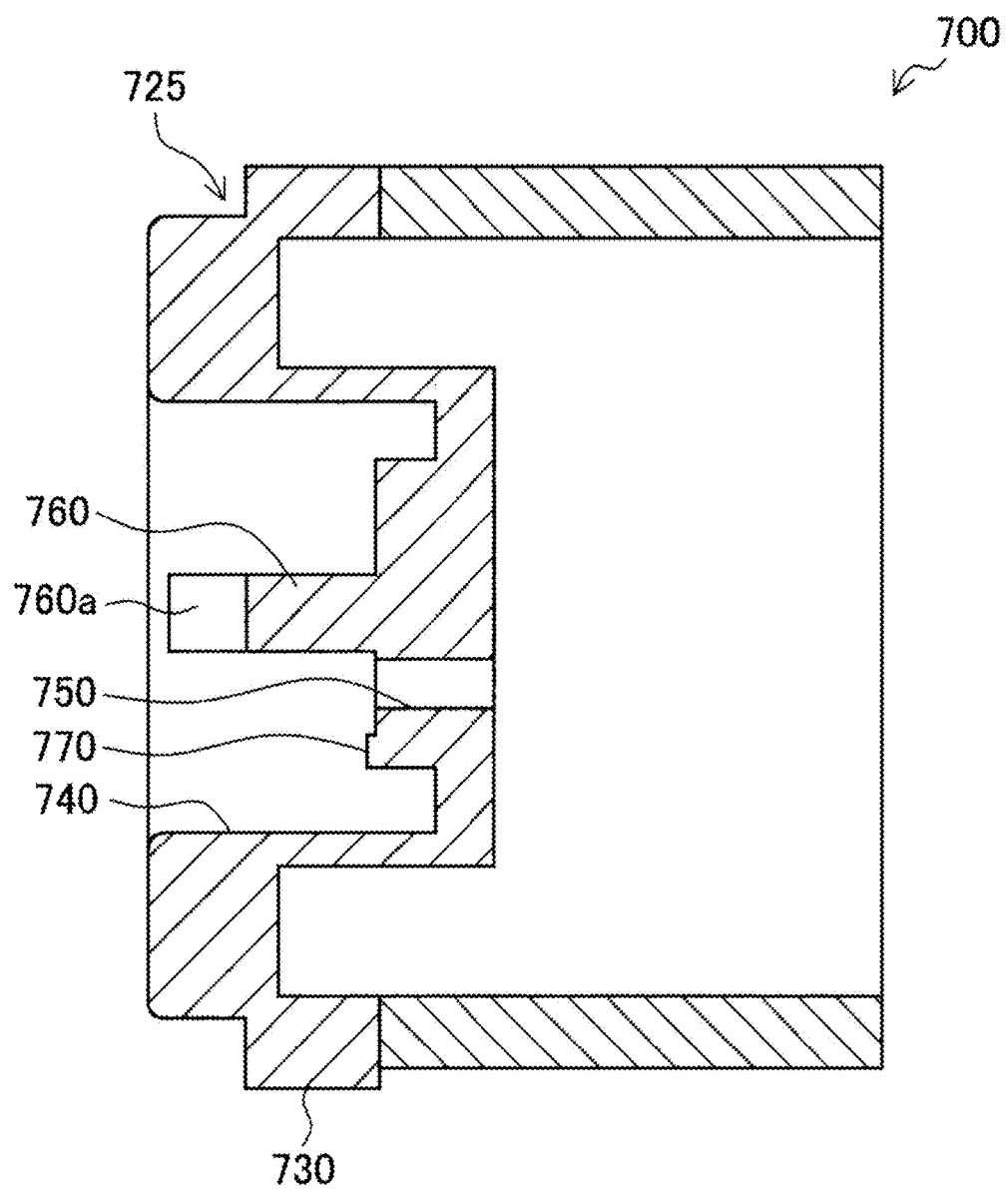
FIG. 17 is an axial cross-sectional view of the second member of the aromatic device according to the same embodiment.

With reference to FIGS. 1 to 17, an aromatic device 1 will be described as an example of a rotary switching device according to an embodiment of the present disclosure. FIG. 1 is a perspective view illustrating the aromatic device 1, FIG. 2 is an exploded perspective view of the aromatic device 1, and FIG. 3 is an axial cross-sectional view illustrating a portion of the aromatic device 1. FIGS. 4 and 5 are explanatory diagrams of a cover 100, FIGS. 6 and 7 are explanatory diagrams of a cartridge case 300, and FIGS. 8 and 9 are explanatory diagrams of a holding part 400. FIGS. 10 and 11 are explanatory diagrams of a perfume cartridge 200, and FIGS. 12 and 13 are explanatory diagrams of a rotating operating part 600. FIGS. 14 and 15 are explanatory diagrams of a prism part 500, and FIGS. 16 and 17 are explanatory diagrams of a base part 700.

In the following description, a direction in which the cover 100 is disposed will be referred to as a front side, and a direction in which the base part 700 is disposed will be referred to as a rear side. FIGS. 4, 6, 8, 10, 12, 14, and 16 are views of respective members seen from the front side, and FIGS. 5, 7, 9, 11, 13, 15, and 17 are axial cross-sectional views of the respective members. Positions of the cross-sections shown in FIGS. 5, 7, 9 11, 13, 15, and 17 are respectively indicated by A to G in FIGS. 4, 6, 8, 10, 12, 14, and 16.

According to the present embodiment, the aromatic device 1 includes the perfume cartridge 200 which is a perfume holding member provided with a plurality of air flow passages 211, 213, 215, 217, and 219 passing therethrough and configured to hold perfume, the base part 700 which is a member having a supply port 750 configured to communicate with some of the air flow passages of the plurality of air flow passages 211, 213, 215, 217, and 219 and introduce air supplied from an air pump which is a wind power source to some of the air flow passages, and a rotation switching mechanism capable of relatively rotating the perfume cartridge 200 so that some of the air flow passages communicating with the supply port 750 are switched.

The aromatic device 1 is one aspect of a rotary switching device and includes the cover 100, the perfume cartridge 200, the cartridge case 300, the prism part 500, the rotating operating part 600, and the base part 700. Among these, the cartridge case 300 corresponds to a first member of the present disclosure, and the base part 700 corresponds to a second member of the present disclosure. Also, the cover 100 corresponds to a third member of the present disclosure. The aromatic device 1 is a device for vaporizing and releasing perfume held in inner circumferential surfaces of the air flow passages 211, 213, 215, 217, and 219 by making air flow to a desired air flow passage selected from the air flow passages 211, 213, 215, 217, and 219 which are a plurality of selection elements provided in the perfume cartridge 200.

The aromatic device 1 may be used, for example, as a device for diffusing a scent into a relatively wide space. Also, unlike a conventional aromatic device, the aromatic device 1 may also be used as a device for releasing a scent over a limited range. For example, a user can release a scent one or more times near his or her face to feel relaxed. In this case, because the scent is not diffused over a wide range, it can be difficult for surrounding people to smell the scent.

A liquid perfume is vaporized and released with air from the air flow passages 211, 213, 215, 217, and 219 in such an aromatic device 1 by air supplied by an air pump (not illustrated) being supplied to the air flow passages 211, 213, 215, 217, and 219 of the perfume cartridge 200. In the aromatic device 1 according to the present embodiment, inner diameters of the air flow passages 211, 213, 215, 217, and 219 are relatively small, and it is difficult to release the perfume to the outside when air is not supplied to the air flow passages 211, 213, 215, 217, and 219.

(1-1-2. Perfume Cartridge)

The perfume cartridge 200 has a main body part 202, an axial direction hole 230, and the plurality of air flow passages 211, 213, 215, 217, and 219. The main body part 202 has a cylindrical outer shape. The main body part 202 is provided with the axial direction hole 230 having an axial center as a center. The axial direction hole 230 may be used as a guide when the cover 100 and the base part 700 are mounted. The outer shape of the perfume cartridge 200 is not limited to being a cylindrical shape. For example, the outer shape of the perfume cartridge 200 may be a cylindrical shape, a rectangular parallelepiped shape, a cubic shape, or any other appropriate shape.

The air flow passages 211, 213, 215, 217, and 219 are formed along the axial direction in the main body part 202. An essential oil or a liquid perfume obtained by diluting an essential oil with ethanol is attached and held, for example, in at least a portion of an inner surface of each of the air flow passages 211, 213, 215, 217, and 219. The air flow passages 211, 213, 215, 217, and 219 are arranged at equal intervals on a circumference around the axial center of the main body part 202. In this way, the air flow passages 211, 213, 215, 217, and 219 to which air flows may be switched by axially rotating the perfume cartridge 200 by a predetermined rotation angle. The number of the air flow passages 211, 213, 215, 217, and 219 is not limited to five.

As a constituent material of the perfume cartridge 200, for example, a polymer resin such as an acrylic resin, a urethane resin, an acrylonitrile-butadiene-styrene (ABS) resin, a polyetherether ketone (PEEK) resin, a polyacetal (POM) resin, a silicone resin, a fluororesin, a cycloolefin polymer resin, and a polyimide resin, a metal such as stainless steel and aluminum, an inorganic crystal such as quartz, a type of glass, or a plurality of materials may be used. However, the constituent material of the perfume cartridge 200 is not limited to the above examples. The perfume cartridge 200 may be manufactured using, for example, a 3D printer, and a material suitable for a 3D printer may be selected as the constituent material of the perfume cartridge 200.

The perfume cartridge 200 has a locking groove 240 on the outer circumferential surface of the main body part 202. The locking groove 240 is used to position the cartridge case 300 and the perfume cartridge 200, together with a locking protrusion part 340 provided at an inner circumferential surface of the cartridge case 300. Also, relative rotation between the cartridge case 300 and the perfume cartridge 200 becomes impossible and the cartridge case 300 and the perfume cartridge 200 may be integrally rotated due to the locking groove 240 and the locking protrusion part 340 being fitted to each other.

The inner diameters of the air flow passages 211, 213, 215, 217, and 219 may be, for example, 10 to 3,000 μm. Particularly, a flow passage having an inner diameter of several tens to several hundreds of μm is also referred to as a "micro flow passage." The air flow passages 211, 213, 215, 217, and 219 having such inner diameters may stably hold a small amount of perfume by having a liquid perfume attached to and held at inner surfaces thereof. Therefore, it is unnecessary for the perfume to be dropped at each time of use. Also, because the perfume cartridge 200 has the air flow passages 211, 213, 215, 217, and 219 having relatively small inner diameters, an outlet opening is small, and a diffusion flux at a time of releasing the scent may be narrowed. Therefore, a user may release a scent over a limited range, e.g., may privately enjoy the scent.

Further, when the air flow passages 211, 213, 215, 217, and 219 have relatively small inner diameters, a high ratio of surface areas to volumes of the air flow passages 211, 213, 215, 217, and 219 can be ensured, and with a small amount of perfume, a highly concentrated perfume may be vaporized and released with air. Further, even when the plurality of air flow passages 211, 213, 215, 217, and 219 are formed so that the air flow passages 211, 213, 215, 217, and 219 have relatively small inner diameters, a size of the outer shape of the perfume cartridge 200 may be reduced so that carrying the perfume cartridge 200 as well as carrying the aromatic device 1 can be facilitated.

The air flow passages 211, 213, 215, 217, and 219 may be provided in a linear shape in the main body part 202 or may be provided in a curved shape in the main body part 202. Alternatively, the air flow passages 211, 213, 215, 217, and 219 may include a partially linear or curved portion. Lengths of the air flow passages 211, 213, 215, 217, and 219 can be increased in the main body part 202 and the amount of held perfume can be increased by the air flow passages 211, 213, 215, 217, and 219 being provided in the curved shape.

A direction of the outlet opening of the air flow passages 211, 213, 215, 217, and 219 may be parallel to the axial direction of the main body part 202 or may be a direction in any other angle. Also, a cross-sectional shape of the air flow passages 211, 213, 215, 217, and 219 is not particularly limited as long as the shape enables a liquid perfume to be attached to and held in the inner surfaces thereof and air can be supplied to the air flow passages 211, 213, 215, 217, and 219. The cross-sectional shape of the air flow passages 211, 213, 215, 217, and 219 may be, for example, a circular shape, an elliptical shape, a quadrilateral shape, a rectangular shape, and any other appropriate shape.

At least one of an inlet opening and the outlet opening of the air flow passages 211, 213, 215, 217, and 219 may have a tapered shape in which a diameter thereof gradually increases toward an opening end thereof. When the outlet opening has a tapered shape, perfume released from the air flow passages 211, 213, 215, 217, and 219 may be easily diffused. Further, when the inlet opening has a tapered shape, a small amount of liquid perfume can be easily injected into the air flow passages 211, 213, 215, 217, and 219, and perfume can be prevented from being attached near an end of the inlet opening and remaining thereon.

Also, the air flow passages 211, 213, 215, 217, and 219 may include a surface increasing part configured to increase a surface in a flow passage. An area to which the liquid perfume is attached is increased and the total amount of held perfume can be increased by providing the air flow passages 211, 213, 215, 217, and 219 with the surface increasing part. Therefore, a total time in which a scent can be released by supplying air to one of the air flow passages 211, 213, 215, 217, and 219 can be extended.

For example, in the surface increasing part, a plurality of cross-shaped components formed along a cross section orthogonal to an axial line of the air flow passages 211, 213, 215, 217, and 219 are connected in the axial direction at cross-shaped crossing portions. Even when the air flow passages 211, 213, 215, 217, and 219 have relatively small diameters, for example, by manufacturing the perfume cartridge 200 using a 3D printer, the surface increasing part can be formed inside the air flow passages 211, 213, 215, and 219. The surface increasing part may be disposed to be rotationally symmetric with respect to the axial center of the air flow passages 211, 213, 215, 217, and 219. Further, the surface increasing part can also be disposed to be translationally symmetric in the axial direction of the air flow passages 211, 213, 215, 217, and 219. Further, the surface increasing part may also be disposed to be mirror symmetric with respect to an arbitrary axis.

The surface increasing part formed in the air flow passages 211, 213, 215, 217, and 219 may have various shapes. For example, a plurality of components formed along a cross-section orthogonal to the axial line of the air flow passages 211, 213, 215, 217, and 219 and intersecting four straight lines may be a surface increasing part connected to an intersecting portion in the surface increasing part in the axial direction. Further, a plurality of cross-shaped components formed along the cross-section orthogonal to the axial line of the air flow passages 211, 213, 215, 217, and 219 may be a surface increasing part connected in the axial direction while being, for example, rotated by 45° at every interval on the corresponding cross-section.

The surface increasing parts may be formed to have a lattice shape having unit sides which have arbitrary inter-axis angles and arbitrary lengths. That is, the surface increasing part may be configured with a combination of a single unit side extending in a diametric direction from the axial center of the air flow passages 211, 213, 215, 217, and 219, another unit side obtained by the rotation of the above unit side by a predetermined angle (90° or 45°), and a plurality of unit lattices formed by the inner surfaces of the air flow passages 211, 213, 215, 217, and 219. Therefore, an equal density of perfume can be held in the air flow passages 211, 213, 215, 217, and 219.

The surface increasing parts can increase surface areas of the inner surfaces of the air flow passages 211, 213, 215, 217, and 219 while maintaining a space through which air passes to not disturb a flux. Therefore, an amount of perfume held inside the air flow passages 211, 213, 215, 217, and 219 may be increased by a liquid perfume being attached to the surfaces and resisting gravity or a flow or air due to wettability, surface tension, and a chemical interaction at an interface.

It is not necessary for the surface increasing part to be rotationally symmetric, translationally symmetric, or mirror symmetric. Further, it is not necessary for the surface increasing part to be constituted by a combination of unit lattices. The surface increasing part may have any shape as long as the shape can be formed without interfering with a flow of air.

Also, when the aromatic device 1 is used as a device for privately enjoying a scent, a straightness of the scent to be released may be improved so that the scent to be released is not diffused over a wide range. For example, the air flow passages 211, 213, 215, 217, and 219 may have spiral grooves on the inner circumferential surfaces thereof. The straightness of air being released by flowing through the air flow passages 211, 213, 215, 217, and 219 may be improved through a gyro effect due to the air flow passages 211, 213, 215, 217, and 219 having the spiral grooves. Alternatively, a tapered portion which has a diameter that is gradually decreased toward an opening end may be provided at the outlet opening of the air flow passages 211, 213, 215, 217, and 219. An air flow speed may be increased and the straightness may be improved due to the outlet opening having the tapered portion.

(1-1-3. Cartridge Case (First Member))

The cartridge case 300 which is the first member holds the perfume cartridge 200 therein. The cartridge case 300 has a cylindrical outer shape. The rear end among both axial ends of the cartridge case 300 is open. The cartridge case 300 has a circular opening 330 having an axial center as a center at a front end side thereof. Further, the cartridge case 300 has holes 311, 313, 315, 317, and 319 configured to respectively communicate with the air flow passages 211, 213, 215, 217, and 219 of the perfume cartridge 200 and formed around the opening 330.

The locking protrusion part 340 extending along the axial direction is provided at the inner circumferential surface of the cartridge case 300. When the perfume cartridge 200 is inserted into the cartridge case 300, the locking protrusion part 340 is disposed in the locking groove 240 provided at the outer circumferential surface of the perfume cartridge 200. In this way, the perfume cartridge 200 and the cartridge case 300 are positioned, and the air flow passages 211, 213, 215, 217, and 219 communicate with the holes 311, 313, 315, 317, and 319. Further, the cartridge case 300 has a plurality of claw parts 341 at the rear end side. The claw parts 341 are formed to have equal intervals by causing positions of the rear end sides of the cartridge case 300 to be different in the axial direction. The number of the claw parts 341 may be equal to the number of the air flow passages 211, 213, 215, 217, and 219 of the perfume cartridge 200.

Predetermined information is displayed on the outer circumferential surface of the cartridge case 300. Such information is used for identifying the air flow passages 211, 213, 15, 217, and 219 which are selection elements. The information may be, for example, at least one of letters, patterns, color schemes, patterns, or the like, that are drawn. With such information, a user of the aromatic device 1 can identify at least the positions of the air flow passages 211, 213, 215, 217, and 219.

Further, at the positions respectively corresponding to the air flow passages 211, 213, 215, 217, and 219, the types of scents held in the air flow passages 211, 213, 215, 217, and 219 may be written in letters. Alternatively, the types of scents held in the air flow passages 211, 213, 215, 217, and 219 may be drawn as drawing patterns. Further, different color schemes or patterns may be displayed in accordance with the positions respectively corresponding to the air flow passages 211, 213, 215, 217, and 219. Because pieces of information are reflected by a mirror surface part 622 and visually recognized by a user from the axial direction, when letters or figures are displayed, the letters or the figures may be displayed in reverse.

Also, because the mirror surface part 622 is formed by a conical part 620, a distance between the outer circumferential surface of the cartridge case 300 and the mirror surface part 622 differs depending on a position in the axial direction. As the distance between the outer circumferential surface of the cartridge case 300 and the mirror surface part 622 is increased, the displayed information is enlarged and visually recognized when viewed from the axial direction of the cartridge case 300. Therefore, when displaying letters, figures, or the like, a size thereof may be determined in consideration of sizes of letters and figures to be visually recognized. The information displayed on the outer circumferential surface of the cartridge case 300 is not limited to the above examples.

A constituent material of the cartridge case 300 is not particularly limited. For example, the constituent material of the cartridge case 300 may be a metal, a resin, a wood, or the like. The cartridge case 300 can be manufactured using, for example, a 3D printer, and a material suitable for a 3D printer may be selected as the constituent material of the cartridge case 300.

(1-1-4. Holding Part)

The holding part 400 holds the rear side of the cartridge case 300. The holding part 400 has a cylindrical outer shape. A front end side among both axial ends of the holding part 400 is open. The holding part 400 has a circular opening 430 having an axial center as a center at a rear end side thereof. Further, the holding part 400 has holes 411, 413, 415, 417, and 419 configured to respectively communicate with the air flow passages 211, 213, 215, 217, and 219 of the perfume cartridge 200 and formed around the opening 430.

The rear end of the cartridge case 300 is inserted into an opening at the front side of the holding part 400. The holding part 400 has a plurality of accommodating recessed parts 441 in which the claw parts 341 of the cartridge case 300 are disposed, formed at the inner circumferential surface thereof. The number of the accommodating recessed parts 441 corresponds to the number of the claw parts 341 and is equal to the number of the air flow passages 211, 213, 215, 217, and 219 of the perfume cartridge 200. In this way, the plurality of air flow passages 211, 213, 215, 217, and 219 respectively communicate with the holes 411, 413, 415, 417, and 419 by the cartridge case 300 holding the perfume cartridge 200 being held at an arbitrary rotation phase in the holding part 400.

Inside the holding part 400, a cushioning member 26 is disposed at an end surface of the rear side of the perfume cartridge 200. The cushioning member 26 has a circular opening 27 having an axial center as a center. Also, the cushioning member 26 has a plurality of holes configured to respectively communicate with the air flow passages 211, 213, 215, 217, and 219 of the perfume cartridge 200 and formed around the opening 27. The cushioning member 26 may have a positioning mechanism for positioning the cushioning member 26 and the perfume cartridge 200 or the holding part 400, or may be attached to the perfume cartridge 200 or the holding part 400 in a state in which the cushioning member 26 is aligned.

A constituent material of the holding part 400 is not particularly limited. For example, the constituent material of the holding part 400 may be a metal, a resin, a wood, or the like. The holding unit 400 can be manufactured using, for example, a 3D printer, and a material suitable for a 3D printer may be selected as the constituent material of the holding unit 400.

(1-1-5. Cover (Third member))

The cover 100 which is a third member is also mounted at the outside of the cartridge case 300. The cover 100 has a cylindrical outer shape. A rear end among both ends in the axial direction of the cover 100 is open. The cover 100 has a scent releasing port 112 configured to communicate with any one of the plurality of air flow passages 211, 213, 215, 217, and 219 of the perfume cartridge 200 and formed at a front end surface thereof. By passing through any one of the air flow passages 211, 213, 215, 217, and 219 of the perfume cartridge 200, air containing a vaporized perfume component is released to the outside through the scent releasing port 112. An inner diameter of the scent releasing port 112 is not particularly limited. However, the inner diameter of the scent releasing port 112 may be at least the same as the inner diameter of the air flow passages 211, 213, 215, 217 and 219 or larger so as not to interfere with a flow of air through the air flow passages 211, 213, 215, 217, and 219 of the perfume cartridge 200.

The scent releasing port 112 serves as an indicating part configured to indicate the selected air flow passages 211, 213, 215, 217, and 219. That is, the scent releasing port 112 may be formed on an end surface at the front side of the cover 100, and the user may recognize the air flow passages 211, 213, 215, 217, and 219 to which air can be supplied by using information displayed at the outer circumferential surface of the cartridge case 300 reflected by the mirror surface part 622 when the aromatic device 1 is seen from the front side in the axial direction.

Inside the cover 100, a cushioning member 22 is disposed at an end surface at the front side of the cartridge case 300. The cushioning member 22 has a circular opening 23 having an axial center as a center. Also, the cushioning member 22 has a hole 24 configured to communicate with the scent releasing port 112 of the cover 100 and formed near the opening 23. The cushioning member 22 may have a positioning mechanism for positioning the cushioning member and the cover 100 or the cartridge case 300, or may be attached to the cover 100 or the cartridge case 300 in a state in which the cushioning member 22 is aligned.

The cover 100 is provided with a fixed shaft 114 extending in the axial direction from an inner surface of an end surface at the front side. The fixed shaft 114 is inserted into the opening 23 of the cushioning member 22, the opening 330 of the cartridge case 300, and the axial direction hole 230 of the perfume cartridge 200. The cover 100 may rotate relative to the cartridge case 300 holding the perfume cartridge 200 about the fixed shaft 114 which is a rotation axis, and the air flow passages 211, 213, 215, 217, and 219 communicating with the scent releasing port 112 are switched in accordance with a relative position of the cover 100. An engaging part 114a formed as a half body cut along an axial center of the fixed shaft 114 is provided at a distal end thereof. The engaging part 114a is fitted to a fixed shaft 760 of the base part 700, and a shape thereof is not limited as long as the shape can be attached to and detached from the fixed shaft 760.

The cover 100 is formed of a base part 110 at a front side and a cylindrical part 120 at a rear side. Of these, the cylindrical part 120 is formed of a transparent material. Therefore, the outer circumferential surface of the cartridge case 300 is visually recognizable from the outside of the cover 100. A method of coupling between the base part 110 and the cylindrical part 120 is not particularly limited. For example, the base part 110 and the cylindrical part 120 may be coupled to each other by an adhesive or may be fixed by a fitting structure.

In the present embodiment, in the cover 100, predetermined information may also be displayed on the cylindrical part 120 formed of a transparent material. Because the cylindrical part 120 is formed of a transparent material, the information displayed on the outer circumferential surface of the cartridge case 300 and the information displayed on the cylindrical part 120 of the cover 100 may be superimposed to be visually recognized by the user. Because it may be impossible for the cover 100 to rotate relative to the cartridge case 300 and the perfume cartridge 200 and the cover 100 is not a part that rotates along with the rotation of the perfume cartridge 200, a display on the cylindrical part 120 of the cover 100 may not enable the air flow passages 211, 213, 215, 217, and 219 to be identified and is not particularly limited. When seen from the axial direction of the cartridge case 300, as a distance between the cover 100 and the mirror surface part 622 is increased, the displayed information is enlarged and visually recognized. Therefore, when letters or figures are displayed, a size thereof may be determined in consideration of sizes of letters and figures to be visually recognized.

A constituent material of the cover 100 is not particularly limited. For example, the constituent material of the cover 100 may be a metal, a resin, a wood, or the like. The cover 100 can be manufactured using, for example, a 3D printer, and a material suitable for a 3D printer may be selected as the constituent material of the cover 100.

(1-1-6. Rotating Operating Part)

The rotating operating part 600 is further disposed outside the cover 100, the cartridge case 300, the perfume cartridge 200, and the holding part 400. The rotating operating part 600 has an outer circumferential cylindrical part 610, the conical part 620, and an inner circumferential cylindrical part 630. The inner circumferential cylindrical part 630 has a locking protrusion part 636 at an inner circumferential surface thereof. The outer circumferential cylindrical part 610 and the inner circumferential cylindrical part 630 are connected via the conical part 620. A large diameter-side end portion of the conical part 620 is connected to an axial central portion of an inner circumferential surface of the outer circumferential cylindrical part 610. Further, a small diameter-side end portion of the conical part 620 is connected to a front-side end portion of the inner circumferential cylindrical part 630.

The cover 100, the cartridge case 300, the perfume cartridge 200, and the holding part 400 are inserted into the inner circumferential cylindrical part 630 of the rotating operating part 600. Here, the locking protrusion part 636 of the inner circumferential cylindrical part 630 is disposed in any one of a plurality of locking groove parts 440 provided at the outer circumferential surface of the holding part 400. In this way, the cartridge case 300 and the perfume cartridge 200 held by the holding part 400 and the holding part 400 can be integrally rotated with the rotating operating part 600. Further, because the cover 100 can rotate relative to the cartridge case 300, the perfume cartridge 200, and the holding unit 400, the rotating operating part 600 and the cover 100 can also rotate relative to each other.

Although the rotating operating part 600 covers an outer periphery of the prism part 500 in the present embodiment, the rotating operating part 600 may not cover the prism part 500. A shape of the rotating operating part 600 is not particularly limited as long as the shape can rotate the perfume cartridge 200, the cartridge case 300, and the holding part 400 arranged inside the aromatic device 1 from the outside. In this case, an outer circumferential surface of the prism part 500 may be surface-processed so that information displayed on the outer surface of the cartridge case 300 is not transmitted therethrough. Alternatively, the outer circumferential surface of the prism part 500 may be exposed to the outside. In this way, the information displayed on the outer circumferential surface of the cartridge case 300 can be visually recognized from the axial direction of the cartridge case 300, and can also be visually recognized from the outer circumferential surface side.

A constituent material of the rotating operating part 600 is not particularly limited. For example, the constituent material of the rotating operating part 600 may be a metal, a resin, a wood, or the like. The rotating operating part 600 can be manufactured using, for example, a 3D printer, and a material suitable for a 3D printer may be selected as a material of the rotating operating part 600.

(1-1-7. Mirror Surface Part)

A surface on a front side of the conical part 620 of the rotating operating part 600 is the mirror surface part 622 on which mirror-finishing is performed. In the present embodiment, the mirror surface part 622 is an inclined surface that is inclined by 45° with respect to the axial direction and specularly reflects information displayed on the cylindrical part 120 of the cover 100 or the information displayed on the outer circumferential surface of the cartridge case 300 that may be visually recognized by being transmitted through the cylindrical part 120 to enable the information to be visually recognized from the front side in the axial direction. A position of a boundary between an end at the front side of the mirror surface part 622, i.e., the mirror surface part 622, and the outer circumferential cylindrical part 610 is almost the same in the axial direction of the rotating operating part 600 as a position of a boundary between the base part 110 and the cylindrical part 120 of the cover 100. Therefore, it is difficult for the base part 110 of the cover 100 to be visually recognized when the mirror surface part 622 is viewed in the axial direction.

Although the mirror surface part 622 is formed with a conical surface in the present embodiment, a shape of the mirror surface part 622 is not limited to this example. For example, the mirror surface part 622 may also be formed with a pyramid surface. Further, the mirror surface part 622 may not be formed continuously throughout 360° and may be formed partially therethrough. Also, a slope of the mirror surface part 622 with respect to the axial direction is not limited to 45°. As long as the information displayed on the outer circumferential surface of the cartridge case 300 which is the first member can be visually recognized from the axial direction, the mirror surface part 622 may be inclined at any appropriate angle.

The mirror surface part 622 is provided by, for example, flattening a front side surface of the conical part 620 and then forming a reflective film formed of a metal, a dielectric, or the like thereon. The reflective film may be formed using, for example, chromium, tantalum, aluminum, or the like. The reflective film is formed by, for example, vapor deposition, printing, coating, plating, or the like. Further, when the conical part 620 is formed of a metal, a surface of the conical part 620 may be processed to be flattened and become a mirror surface.

The mirror surface part 622 may not be integrated with the rotating operating part 600 and may be provided as a separate member. That is, as long as the mirror surface part 622 is disposed at least near the outer circumferential surface of the cartridge case 300 on which predetermined information is displayed and is formed by a surface intersecting the axial direction of the cartridge case 300, other configurations thereof are not particularly limited.

(1-1-8. Prism Part)

The prism part 500 is disposed inside the outer circumferential cylindrical part 610 at a side thereof in front of the mirror surface part 622. The prism part 500 may be lightly press-fitted into the outer circumferential cylindrical part 610 or may be coupled thereto by an appropriate means. The prism part 500 has a main body part 510 formed of a transparent material and an axial direction hole 530 provided in the main body part 510 and having an axial center as a center. The axial direction hole 530 has a tapered shape having a cross-sectional area that gently gradually expands toward a front side thereof. In this way, the cover 100, the cartridge case 300, the holding part 400, and the like can be easily inserted from the front side when the perfume cartridge 200 is mounted. Also, when the prism part 500 is molded by a resin, the prism part 500 can be easily withdrawn from a mold.

The cover 100, the cartridge case 300, and the perfume cartridge 200 are disposed in the axial direction hole 530 of the prism part 500. The main body part 510 of the prism part 500 is formed of a transparent material and does not hinder the information displayed on the cylindrical part 120 of the cover 100 that is specularly reflected at the mirror surface part 622 and may be visually recognized from the axial direction or the information displayed on the outer circumferential surface of the cartridge case 300 from being visually recognized. Introduction of dust and the like into the rotating operating part 600 can be reduced by the prism part 500 being disposed between the cover 100 and the rotating operating part 600.

A constituent material of the prism part 500 is not particularly limited as long as the prism part 500 is transparent after being formed. For example, the prism part 500 may be formed of a glass, a crystal, a transparent resin, or the like. Further, the axial direction hole 530 of the prism part 500 is not limited to being a tapered shape having a cross-sectional area that gradually increases toward the front side. The axial direction hole 530 of the prism part 500 may have a constant cross-sectional area, or may have a tapered shape having a cross-sectional area that gradually increases toward the rear side. When the cross-sectional area of the axial direction hole 530 has a tapered shape that gradually expands toward the rear side, introduction of dust and the like from the outside (the front side) of the aromatic device 1 can be further reduced.

(1-1-9. Base Part (Second Member))

The rotating operating part 600, the cover 100, the perfume cartridge 200, the cartridge case 300, the holding part 400, and the like are supported by the base part 700 which is the second member. The base part 700 has a concave part 740 having a circular cross-section, into which the inner circumferential cylindrical part 630 of the rotating operating part 600 is inserted, formed at a central portion of a front side surface thereof. Also, the base part 700 has a ring-shaped stepped part 725 in which the outer circumferential cylindrical part 610 of the rotating operating part 600 is disposed, formed on an outer edge portion of the front side surface. The outer circumferential cylindrical part 610 is disposed in the stepped part 725, the inner circumferential cylindrical part 630 of the rotating operating part 600 is disposed in the concave part 740, and the holding part 400, the perfume cartridge 200, and the like are disposed inside the inner circumferential cylindrical part 630.

The base part 700 has the fixed shaft 760 erected on a bottom surface of the concave part 740 and extending toward the front side. The fixed shaft 760 is inserted into the opening 430 of the holding part 400 and the axial direction hole 230 of the perfume cartridge 200. For example, the fixed shaft 760 is lightly press-fitted into the axial direction hole 230 of the perfume cartridge 200. In this way, the rotating operating part 600, the cover 100, the perfume cartridge 200, the cartridge case 300, the holding part 400, and the like are supported by the base part 700.

An engaging part 760a formed of a half body cut along an axial center thereof is provided at a distal end of the fixed shaft 760. The engaging part 760a of the fixed shaft 760 is fitted to the engaging part 114a at a distal end of the fixed shaft 114 of the cover 100 in the axial direction hole 230 of the perfume cartridge 200 in a state of being axially rotated by 180°. In this way, relative rotation between the cover 100 and the base part 700 becomes impossible. As a result, the rotating operating part 600, the perfume cartridge 200, the cartridge case 300, and the holding part 400 can rotate relative to the base part 700. However, like the engaging part 114a of the cover 100, the engaging part 760a may be fitted to the fixed shaft 114 of the cover 100 and have any shape that may be attached to and detached from the fixed shaft 114, and the shape is not limited to the above shape.

Further, the base part 700 has the air supply port 750 on the bottom surface of the concave part 740. The base part 700 includes an air pump (not illustrated), a battery, a circuit board, and the like therein. The air pump is an example of a blower, is driven by electric power supplied from the battery, and introduces air into the air supply port 750. The air pump may be, for example, a diaphragm type pump which deforms a diaphragm by supplying an alternating current to a piezoelectric element and performs air suctioning and pumping. The battery may be a battery that is only discharged and is replaceable, or may be a rechargeable battery that can be charged and discharged. An operation of turning on or turning off the air pump is performed by operating a switch operating part 730. For example, by pressing the switch operating part 730, a switching element of the circuit board is electrically connected, and power is supplied from the battery to the air pump. In this way, air flows to the perfume cartridge 200 via the air supply port 750.

For example, an on/off state of energization may be switched every time the switch operating part 730 is pushed downward, and the energization may be maintained in the on-state while the switch operating part 730 is pressed downward. Other electronic components such as a light source, such as a light emitting diode (LED), configured to indicate an operational state of the aromatic device 1 may be mounted on the circuit board. Further, a communication device may be mounted on the circuit board to enable the aromatic device 1 to be operated by a remote controller, a smart phone, or the like.

The blower configured to supply air toward the perfume cartridge 200 is not limited to being an air pump. For example, the blower may be a blower of a type in which a fan is rotated. Further, the blower configured to supply air to the perfume cartridge 200 may not be an electrically driven type, and may be of a manual type. When a means for supplying air is a manual type of means, the battery, the switch operating part 730, and the circuit board may be omitted.

Further, a protruding part 770 for positioning is provided on the bottom surface of the concave part 740. The protruding part 770 is locked to the locking groove part 440 of the holding part 400 in which the locking protrusion part 636 of the rotating operating part 600 is disposed. On the outer circumferential surface of the holding part 400, the same number of locking groove parts 440 as the number of the air flow passages 211, 213, 215, 217, and 219 of the perfume cartridge 200 are provided at equal intervals. One of the air flow passages 211, 213, 215, 217, and 219 communicates with the air supply port 750 in a state in which the protruding part 770 is locked to one of the locking groove parts 440. Therefore, the air flow passages 211, 213, 215, 217, and 219 communicating with the air supply port 750 are switched by the rotating operating part 600 being rotated.

The protruding part 770 may be biased forward by a spring or the like. That is, when the protruding part 770 is retracted due to the spring being contracted or the like and any one of the locking groove parts 440 corresponds to the position of the protruding part 770 while the perfume cartridge 200 is being rotated, the protruding part 770 may protrude toward the locking groove part 440. In this way, the holding part 400, the rotating operating part 600, or the like can be rotated without switching a distance between the base part 700, the holding part 400, and the like.

A constituent material of the base part 700 is not particularly limited. For example, the constituent material of the base part 700 may be a metal, a resin, a wood, or the like. The base part 700 can be manufactured using, for example, a 3D printer, and a material suitable for a 3D printer may be selected as a material of the base part 700.

(1-1-10. System Configuration Example)

Figure 18:
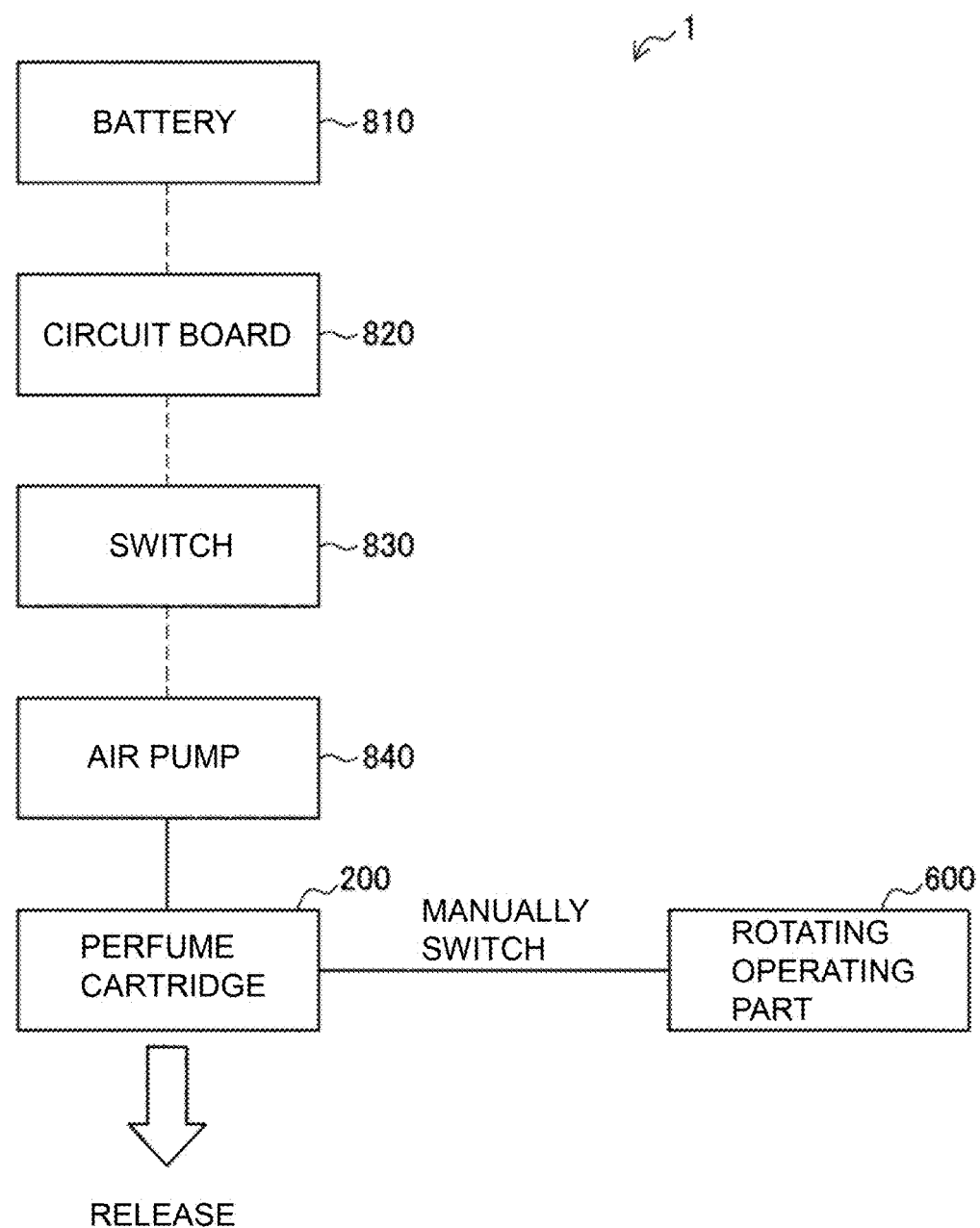
FIG. 18 is a block diagram illustrating an example of a system configuration of an aromatic device.

Next, a system configuration of the aromatic device 1 according to the present embodiment will be briefly described. FIG. 18 illustrates an example of a system block diagram of the aromatic device 1. A battery 810 is electrically connected to an air pump 840 via a circuit board 820 and a switching element 830. Power of the battery 810 is supplied to the air pump 840 according to operation of the switch operating part 730. When the air pump 840 is driven and air flows through the air flow passages 211, 213, 215, 217, and 219 of the perfume cartridge 200, perfume held in the inner surfaces of the air flow passages 211, 213, 215, 217, and 219 is vaporized, and a scent is released with air. Also, in the example of FIG. 18, the rotating operating part 600 is manually rotated, and the air flow passages 211, 213, 215, 217, and 219 of the perfume cartridge 200 in to which air supplied from the air pump 840 is introduced may be switched.

Figure 19:
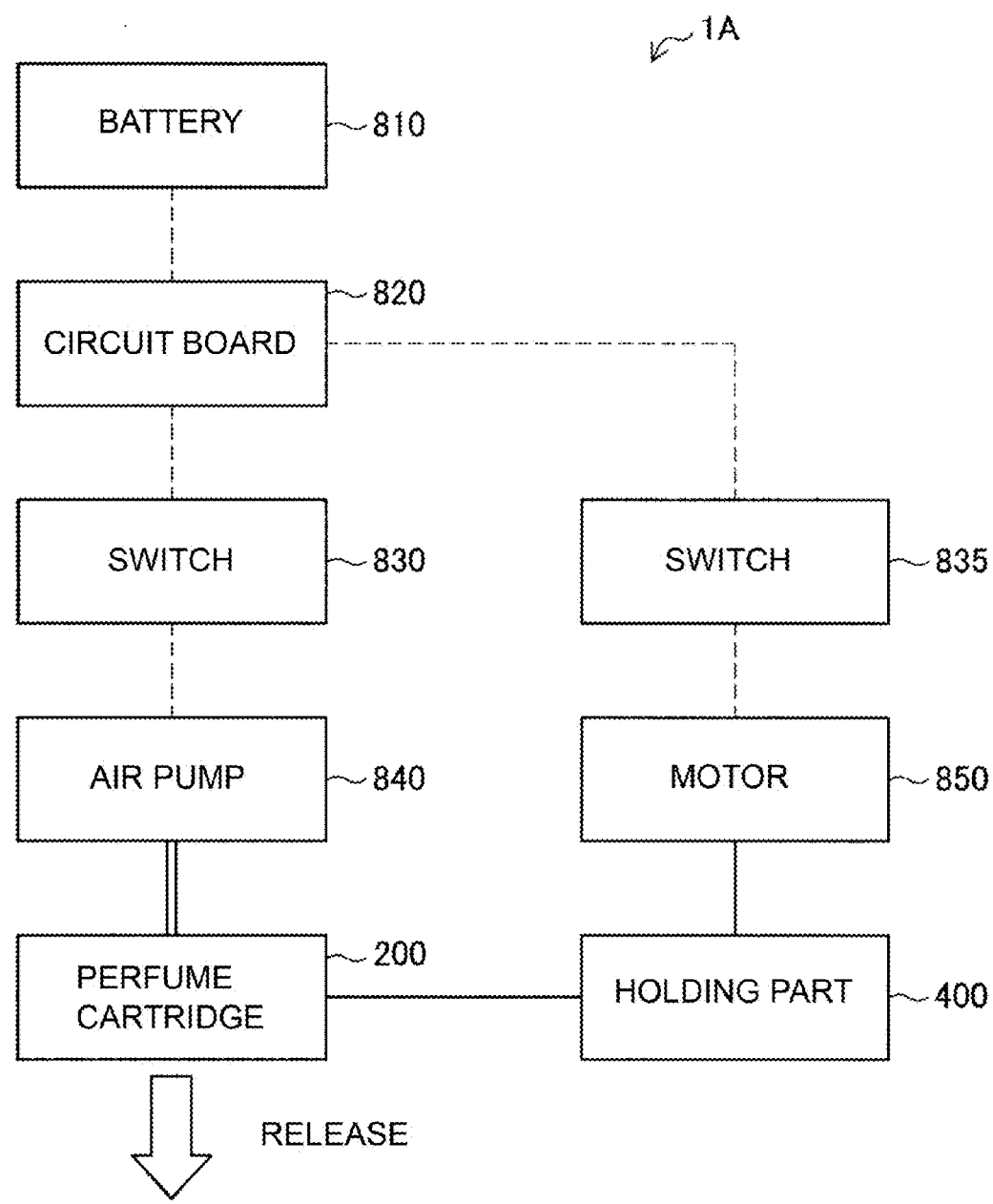
FIG. 19 is a block diagram illustrating another example of a system configuration of an aromatic device.

FIG. 19 illustrates an example of a system block diagram of a different aromatic device 1A. In the example illustrated in FIG. 19, the rotating operating part 600, the cartridge case 300, or the holding part 400 is rotated by a motor 850, and the air flow passages 211, 213, 215, 217, and 219 of the perfume cartridge 200 into which air supplied from the air pump 840 is introduced may be switched.

<1-2. Summary>

As described above, in the aromatic device 1 according to the first embodiment, the cylindrical cartridge case (the first member) 300 configured to hold the perfume cartridge 200 and integrally rotate with the perfume cartridge 200 is supported to be axially rotatable with respect to the base member (the second member) 700 having the air supply port 750. Also, depending on relative positions between the perfume cartridge 200 or the cartridge case 300 and the base part 700, the air flow passages 211, 213, 215, 217, and 219 communicating with the air supply port 750 and communicating with the scent releasing port 112 are switched.

Information for identifying the air flow passages 211, 213, 215, 217, and 219 is displayed on the outer circumferential surface of the cartridge case 300. Such information is reflected by the mirror surface part 622 disposed near the outer circumferential surface of the cartridge case 300 and can be visually recognized from the axial direction of the cartridge case 300. Therefore, the user can recognize a position at which each of the air flow passages 211, 213, 215, 217, 219 is located when viewing the aromatic device 1 from the axial direction.

Also, the scent releasing port 112 which is the indicating part provided in the cover 100 is also visually recognized when the aromatic device 1 is viewed from the axial direction. Therefore, the user can easily change the air flow passages 211, 213, 215, 217, and 219 so that desired air flow passages 211, 213, 215, 217, and 219 communicate with the scent releasing port 112 by the rotating operating part 600 being rotated while the aromatic device 1 is viewed from the axial direction. In the present embodiment, the axial direction refers to a direction in which a scent is released, and the user may change the air flow passages 211, 213, 215, 217, and 219 by releasing a scent and checking the scent.

Also, in the aromatic device 1 according to the present embodiment, information is also displayed on the cylindrical part 120, which is formed of a transparent material, of the cover 100. Because the cylindrical part 120 is formed of a transparent material, information displayed on the outer circumferential surface of the cartridge case 300 and information displayed on the cylindrical part 120 of the cover 100 may be superimposed to be visually recognized by the user. Therefore, designability can be improved, and satisfaction of the user can be improved.

Furthermore, the aromatic device 1 according to the present embodiment includes the perfume cartridge 200 having the air flow passages 211, 213, 215, 217, and 219 which have both ends opened and a perfume held in at least a portion of the inner surfaces thereof. The perfume cartridge 200 has the air flow passages 211, 213, 215, 217, and 219 having relatively small inner diameters, and can stably hold a small amount of perfume. The perfume cartridge 200 has the air flow passages 211, 213, 215, 217, and 219 having relatively small inner diameters, and by supplying air to the air flow passages 211, 213, 215, 217, and 219, the perfume is vaporized and released with the air. Here, because an outlet opening through which a scent is released is relatively small, a diffusion flux of the released scent may be narrowed. Also, because a ratio of surface areas to volumes of the air flow passages 211, 213, 215, 217, and 219 is high, a highly concentrated perfume may be vaporized with a small amount of perfume. Therefore, the aromatic device 1 according to the present embodiment may release a highly concentrated scent over a narrow range when used, for example, to privately enjoy the scent.

Also, because the perfume cartridge 200 has the air flow passages 211, 213, 215, 217, and 219 having relatively small inner diameters, the size of the outer shape of the perfume cartridge 200 may be reduced so that carrying the perfume cartridge 200 or carrying the aromatic device 1 can be facilitated. Also, the perfume cartridge 200 holds perfume in the air flow passages 211, 213, 215, 217, and 219, and it is unnecessary for the perfume to be dropped at each time of use.

Further, in the aromatic device 1 according to the present embodiment, the perfume cartridge 200 may be replaced. In this way, the perfume cartridge 200 in which perfume having an appropriate scent can be selected depending on a use situation or a preference of a user. Therefore, the aromatic device 1 may be used in various situations such as enjoying a different type of scent or switching a degree of diffusion of a scent. In this case, by replacing the cartridge case 300 together with the perfume cartridge 200, a desired scent can be easily selected while types of perfumes held in the air flow passages 211, 213, 215, 217, and 219 are visually recognized.

2. Second Embodiment

A rotary switching device according to the present disclosure can be modified and applied in various ways. Hereinafter, a rotary switching device according to the second embodiment of the present disclosure will be described.

Figure 20:
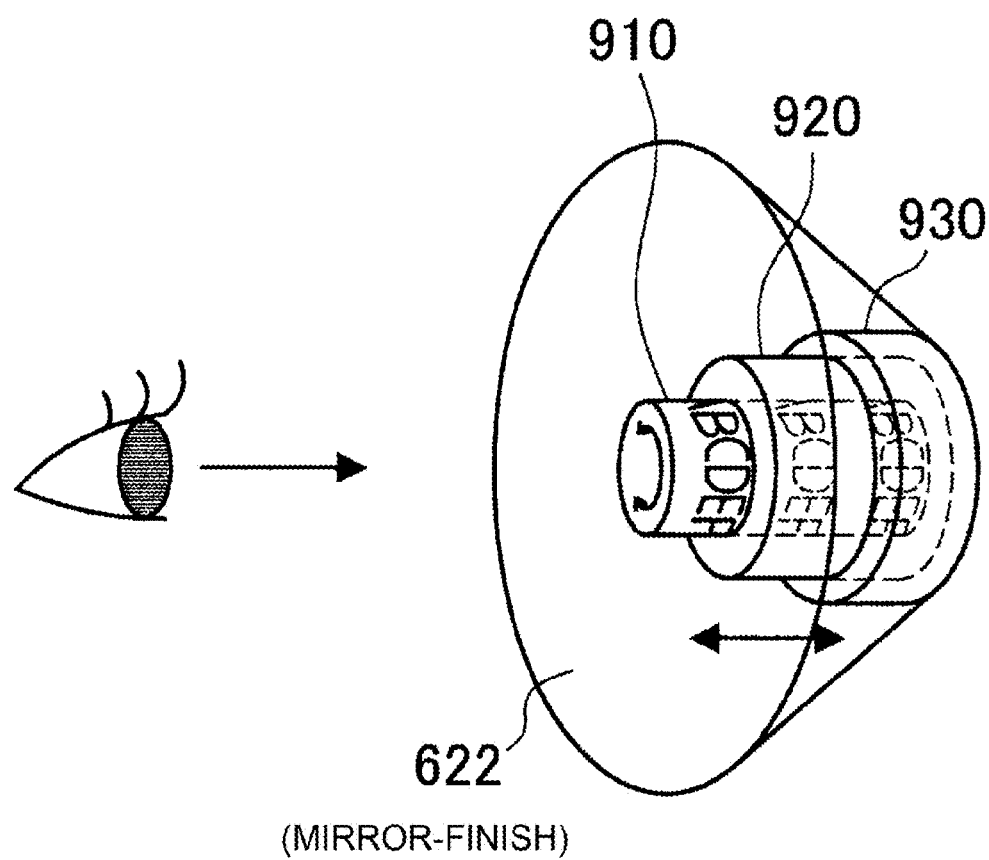
FIG. 20 is an explanatory diagram illustrating an aromatic device which is a rotary switching device according to a second embodiment of the present disclosure.

FIG. 20 is an explanatory diagram illustrating the rotary switching device according to the second embodiment. In the example, the rotary switching device includes a first cylindrical member 910 corresponding to the cartridge case 300 of the aromatic device 1 according to the first embodiment, a second cylindrical member 920 corresponding to the cylindrical part 120 of the cover 100, the mirror surface part 622, and a third cylindrical member 930. The third cylindrical member 930 corresponds to a fourth member of the present disclosure. In FIG. 20, other members corresponding to members such as the base part 110 of the cover 100, the plurality of holes 311, 313, 315, 317, and 319 of the cartridge case 300, the prism part 500, the rotating operating part 600, and the base part 70 are omitted to facilitate understanding.

The third cylindrical member 930 which is the fourth member is a cylindrical member formed of a transparent material. The third cylindrical member 930 is further disposed outside an outer circumferential surface of the second cylindrical member 920 and is movable along an axial direction. Because the third cylindrical member 930 is formed of a transparent material, information displayed on an outer circumferential surface of the first cylindrical member 910, which can be reflected by the mirror surface part 622, is visually recognized in the axial direction of the first cylindrical member 910 via the second cylindrical member 920 and the third cylindrical member 930. Here, the information displayed on the outer circumferential surface of the first cylindrical member 910 is visually recognized by a user by being superimposed with information displayed on the second cylindrical member 920 and the third cylindrical member 930.

Also, a distance between the third cylindrical member 930 and the mirror surface part 622 is varied according to an axial position of the third cylindrical member 930. As the distance between the third cylindrical member 930 and the mirror surface part 622 increases, the displayed information is enlarged and visually recognized when viewed from the axial direction of the first cylindrical member 910. Therefore, a method by which a user visually recognizing the displayed information may be switched and designability can be further improved by adjusting the axial position of the third cylindrical member 930.

Figure 21:
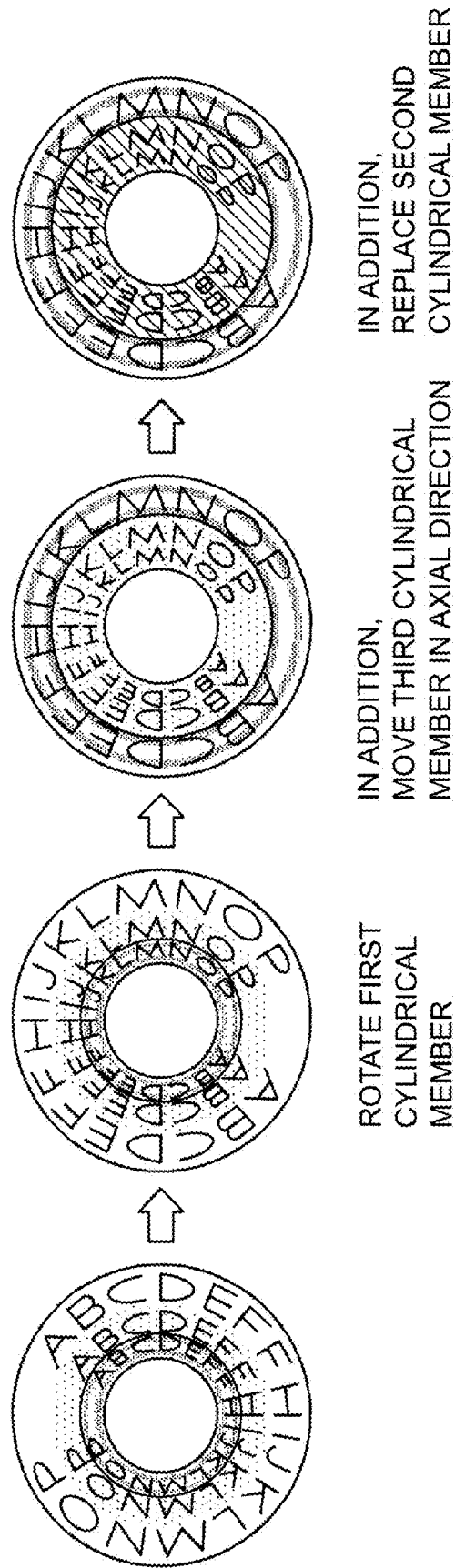
FIG. 21 is an explanatory diagram illustrating a method of visually recognizing information by using the aromatic device according to the same embodiment.

FIG. 21 is a view for describing a method of visually recognizing information when the rotary switching device according to the present embodiment is viewed from the axial direction. As illustrated in FIG. 20, letters are written by being vertically and horizontally inverted on the first cylindrical member 910, which is divided into three stages in the axial direction. Also, the second cylindrical member 920 is disposed outside the outer circumferential surface in a range of two-thirds of a rear side of the first cylindrical member 910. It may be impossible for the second cylindrical member 920 to move in the axial direction. Color schemes or patterns are displayed on the second cylindrical member 920. Further, the third cylindrical member 930 is disposed outside the outer circumferential surface at the rear side of the second cylindrical member 920. A position of the third cylindrical member 920 can be adjusted over an entire axial range of the first cylindrical member 910. In the third cylindrical member 930, a double line that is a 360° circle is drawn.

The leftmost view in FIG. 21 illustrates a visual recognition method when the third cylindrical member 930 is disposed at the rearmost side as illustrated in FIG. 20. Among the letters written in the three stages on the first cylindrical member 910, letters at an outside in a diametric direction which are visually recognized after letters written at the front side of the first cylindrical member 910 are reflected appear to be the largest. Conversely, among the letters written in the three stages on the first cylindrical member 910, letters at an inside in the diametric direction which are visually recognized after letters written at the rear side of the first cylindrical member 910 are reflected appear to be the smallest. Also, color schemes or patterns displayed on the second cylindrical member 920 is superimposed on a letter portion at a second stage at the inside in the diametric direction. Further, the double line drawn on the third cylindrical member 930 is superimposed on a letter portion at the innermost side in the diametric direction.

When the first cylindrical member (the first member) 910 is axially rotated, positions of the letters written on the first cylindrical member 910 are rotated. In the example of FIG. 21, because the first cylindrical member 910 is rotated by 180°, the positions of the letters move 180°. Further, when the axial position of the third cylindrical member 930 is moved to the front side of the first cylindrical member 910, the double line drawn on the third cylindrical member 930 is superimposed on the outermost letter portion in the diametric direction. Here, an interval between the double lines appears to be wide, and a thickness of the line also appears to be thick. Furthermore, when the second cylindrical member 920 is replaced with a member having a different color scheme or pattern, a color scheme or pattern which is superimposed on the outermost letter portion and is seen is also switched.

In this way, the rotary switching device according to the present embodiment can change a method through which information is visually recognized by a user and can improve user satisfaction due to high designability. The third cylindrical member 930 may be attached to the second cylindrical member 920, or may be attached to a surrounding member such as the mirror surface part 622. Further, the third cylindrical member 930 may be integrally rotatable with the first cylindrical member 910, or may be integrally rotatable with the second cylindrical member 920. Further, in the rotary switching device according to the present embodiment, the second cylindrical member 920 may not be provided.

3. Third Embodiment

Next, an aromatic device which is a rotary switching device according to a third embodiment of the present disclosure will be described. The aromatic device according to the present embodiment differs from the aromatic device according to the first embodiment in a configuration for switching air flow passages through which air passes. Hereinafter, with respect to the aromatic device according to the present embodiment, points different from the aromatic device according to the first embodiment will be mainly described. Also, in the following description, an example of a detaching mechanism of a cartridge assembly will be described.

(3-1. Overall Configuration)

Figure 22:
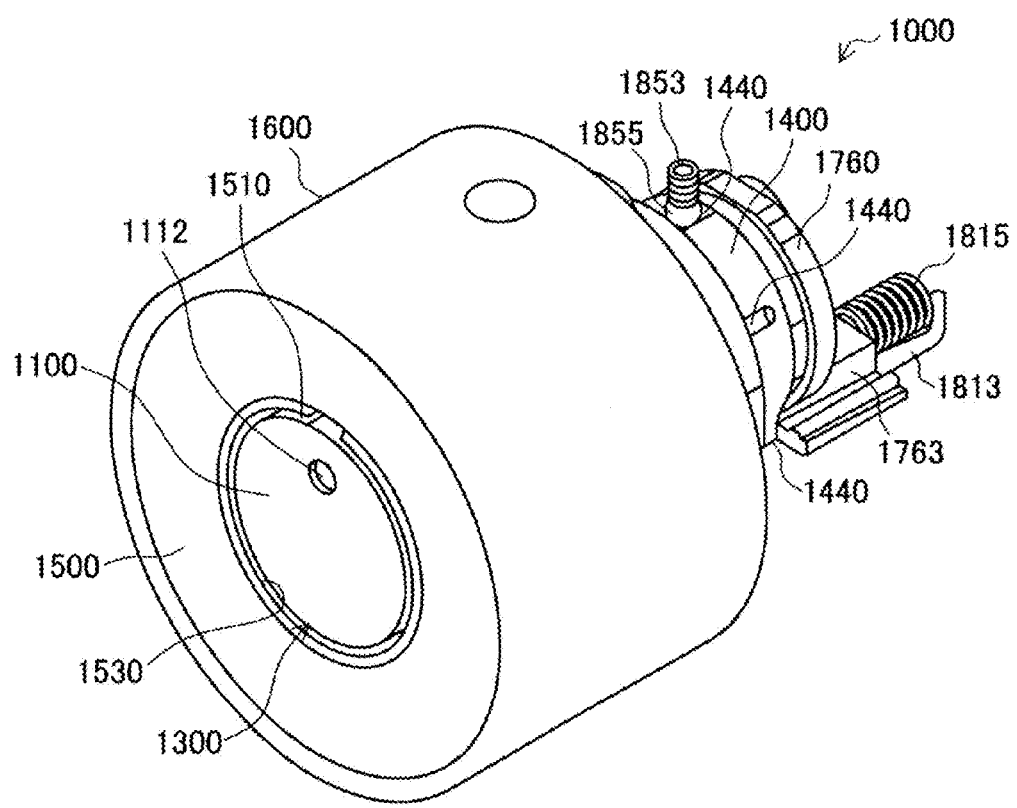
FIG. 22 is a perspective view illustrating a portion of an aromatic device according to a third embodiment of the present disclosure.
Figure 23:
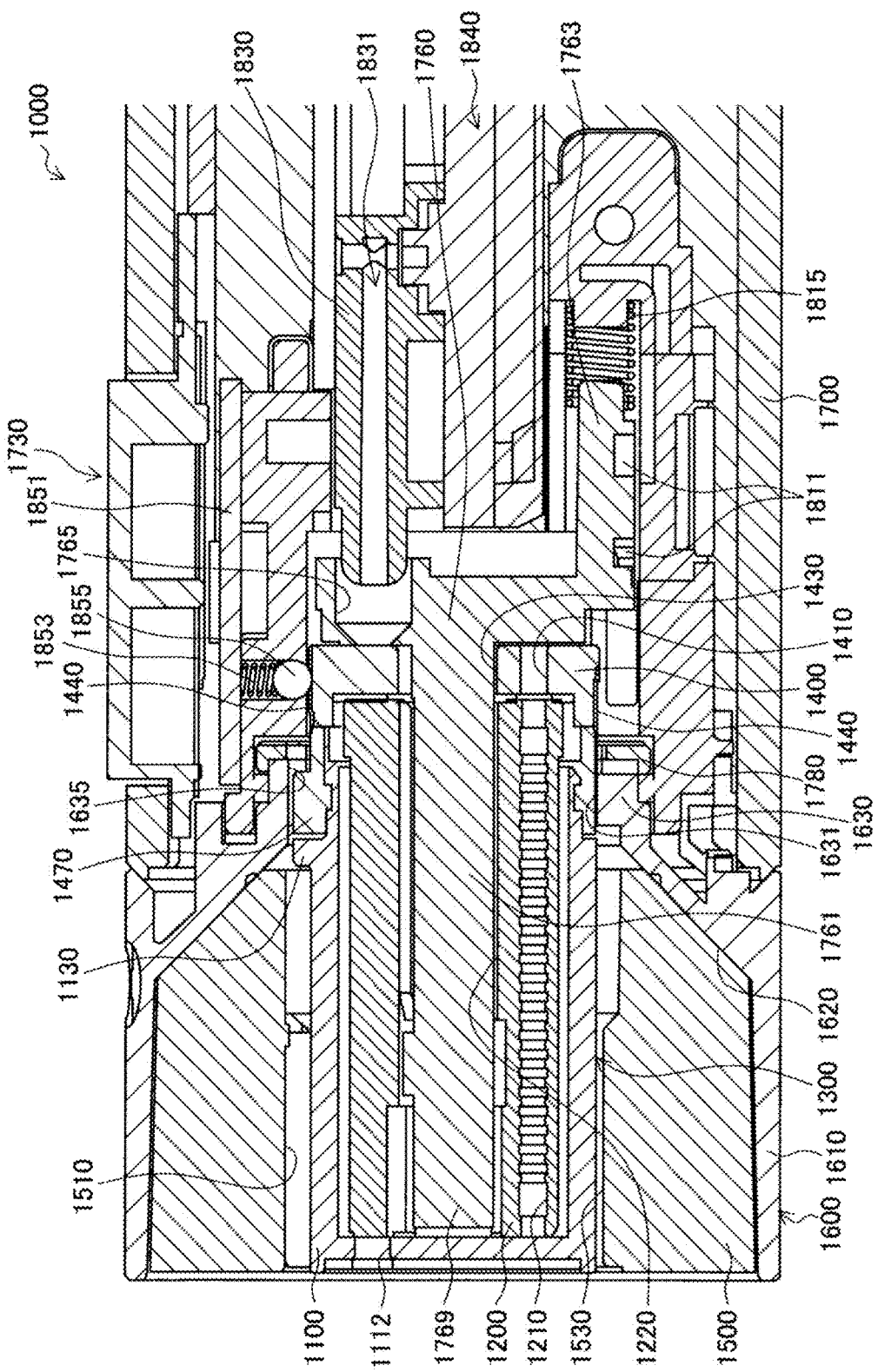
FIG. 23 is an axial cross-sectional view illustrating a portion of the aromatic device which is the rotary switching device according to the same embodiment.
Figure 24:
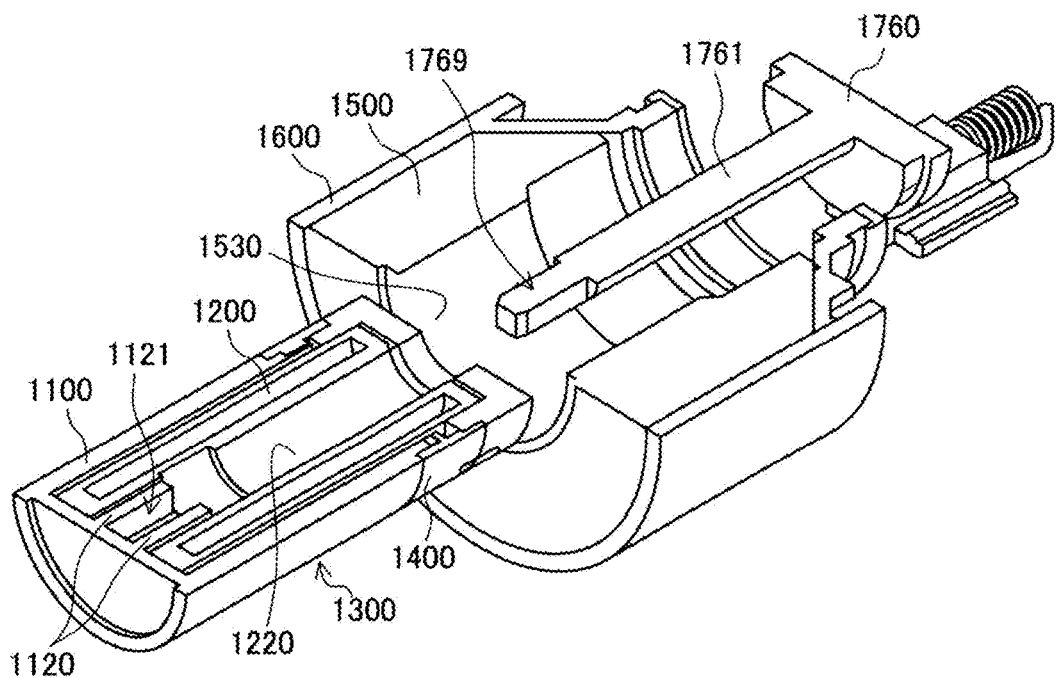
FIG. 24 is an exploded perspective view illustrating a portion of the aromatic device in half according to the same embodiment.

First, referring to FIGS. 22 to 24, an overall configuration of an aromatic device 1000 according to the present embodiment will be described. FIG. 22 is a perspective view illustrating a portion of the aromatic device 1000, and FIG. 23 is an axial cross-sectional view illustrating the portion of the aromatic device 1000. In addition, FIG. 24 is an exploded perspective view illustrating the portion of the aromatic device 1000.

The aromatic device 1000 according to the present embodiment includes a perfume cartridge 1200 which is a perfume holding member provided with a plurality of air flow passages 1210 passing therethrough and configured to hold perfume, a base part 1760 which is a member having a supply port 1765 configured to communicate with some of the plurality of air flow passages 1210 and introduce air supplied from an air pump 1840 as a wind power source to some of the air flow passages, and a rotary switching mechanism capable of relatively rotating the perfume cartridge 1200 so that some of the air flow passages communicating with the supply port 1765 are switched.

The aromatic device 1000 according to the present embodiment includes a cover 1100, the perfume cartridge 1200, a prism part 1500, a rotating operating part 1600, the base part 1760, and a case body 1700. The aromatic device 1000 is a device that supplies air to the desired air flow passage 1210 selected from the five air flow passages 1210 which are a plurality of selection elements provide in the perfume cartridge 1200 which is a first member to vaporize perfume held in a moist state and releasing a scent. Specifically, in the aromatic device 1000, a perfume is vaporized and released from the air flow passages 1210 together with air by supplying air supplied from the air pump 1840 to the air flow passages 1210 of the perfume cartridge 1200. The air pump 1840 is driven by operating a switch operating part 1730 provided at the case body 1700.

In the aromatic device 1000 according to the present embodiment, a cartridge assembly 1300 is formed by the cover 1100, the perfume cartridge 1200, and a holding part 1400. The cartridge assembly 1300 is supported by the base part 1760. In the cartridge assembly 1300, the perfume cartridge 1200 and the holding part 1400 are supported to be rotatable relative to the base part 1760. On one hand, it may be impossible for the cover 100 to rotate relative to the base part 1760. In the aromatic device 1000 according to the present embodiment, the perfume cartridge 1200 corresponds to the first member of the present disclosure, the base part 1760 corresponds to the second member of the present disclosure, and the cover 1100 corresponds to the third member of the present disclosure.

In the aromatic device 1000 according to the present embodiment, predetermined information is displayed on an outer circumferential surface of the perfume cartridge 1200. Such information is used for identifying the air flow passages 1210 which are selection elements. The information may be the information exemplified in the first embodiment or the second embodiment.

The cover 1100 has a cylindrical outer shape, and an end at a rear side thereof is open. The cover 1100 holds the perfume cartridge 1200 therein. The cover 1100 has a scent releasing port 1112 configured to communicate with any one of the air flow passages 1210 of the perfume cartridge 1200 and formed on an end face at a front side. Air containing a vaporized perfume component is released to the outside through the scent releasing port 1112 by passing through any one of the air flow passages 1210 of the perfume cartridge 1200. The holding part 1400 is fitted to an end at a rear side of the cover 1100. The cover 1100 is formed of a transparent material, and information displayed on the outer circumferential surface of the perfume cartridge 1200 may be visually recognized from the outside of the cover 1100. The cover 1100 has a protruding part 1130 formed at a portion of an outer circumferential surface thereof at the rear side.

Predetermined information may also be displayed on the cover 1100 formed by a transparent material. Because the cover 1100 is formed of a transparent material, information displayed on the outer circumferential surface of the perfume cartridge 1200 and information displayed on the cover 1100 may be superimposed to be visually recognized by a user.

Further, the cover 1100 has a pair of erecting parts 1120 extending along the axial direction at an inner surface of the end surface at the front side. An accommodating part 1121 is formed between the pair of erecting parts 1120. A rotation preventing part 1769 provided at a distal end of a shaft part 1761 of the base part 1760, which is a support shaft of the cartridge assembly 1300, is inserted into the accommodating part 1121. A circumferential cross-sectional shape of the rotation preventing part 1769 is a non-circular shape, and a circumferential cross-sectional shape of the accommodating part 1121 is almost the same as that of the rotation preventing part 1769. In this way, relative rotation between the cover 1100 and the base part 1760 is prevented.

The holding part 1400 is fitted into the end at the rear side of the cover 1100 and holds the rear end side of the perfume cartridge 1200. The holding part 1400 and the cover 1100 are coupled to be relatively rotatable. When the holding part 1400 and the cover 1100 relatively rotate, the perfume cartridge 1200 rotates in synchronization with the holding part 1400. The holding part 1400 has a protruding part 1470 that may be continuous with the protruding part 1130 of the cover 1100 and formed at a portion of an outer circumferential surface at a front side. Also, the holding part 1400 has a plurality of groove parts 1440 at the outer circumferential surface thereof. In the example of the aromatic device 1000 according to the present embodiment, six groove parts 1440 are provided at 60° intervals around an axial center thereof. Positions of five of the groove parts 1440 of the six groove parts 1440 correspond to positions of the air flow passages 1210 of the perfume cartridge 1200 held therein. That is, the five air flow passages 1210 provided in the perfume cartridge 1200 are provided at 60° intervals around the axial center.

A locking member 1855 biased toward the groove part 1440 from a surrounding portion of the holding part 1400 by a spring 1853 can enter the groove part 1440. Like the cover 1100, the spring 1853 and the locking member 1855 do not rotate in synchronization with the holding part 1400, and the locking member 1855 can enter any one of the groove parts 1440 according to a rotational position of the holding part 1400. In this way, a user can obtain a feeling of a click when rotating the perfume cartridge 1200 and the holding part 1400. Further, in a state in which predetermined rotational positions of the perfume cartridge 1200 and the holding part 1400 are determined, positional deviation can be prevented.

Further, the holding part 1400 has a circular opening 1430 having an axial center as a center. Five holes 1410 configured to respectively communicate with the air flow passages 1210 of the perfume cartridge 1200 are provided near the opening 1430. That is, the five holes 1410 are provide at 60° intervals around an axial circumference. Therefore, the air flow passages 1210 to which air supplied from the air pump 1840 is supplied may be switched by relatively rotating the perfume cartridge 1200 and the holding part 1400 with respect to the base part 1760.

The rotating operating part 1600 is further disposed at an outer circumference of the cartridge assembly 1300. The rotating operating part 1600 includes an outer circumferential cylindrical part 1610, a conical part 1620, and an inner circumferential cylindrical part 1630. The outer circumferential cylindrical part 1610 and the inner circumferential cylindrical part 1630 are connected via the conical part 1620. A surface at a front side of the conical part 620 is a mirror surface part on which mirror-finishing is performed.

The inner circumferential cylindrical part 1630 has an axial groove 1635 in a portion of an inner circumferential surface thereof. The protruding part 1470 provided at the outer circumferential surface of the holding part 1400 of the cartridge assembly 1300 is disposed in the axial groove 1635. Therefore, by rotating the rotating operating part 1600, the protruding part 1470 in the axial groove 1635 is rotated, and the holding part 1400 and the perfume cartridge 1200 rotate in synchronization with the rotating operating portion 1600.

Also, when the rotating operating part 1600 is rotated, the protruding part 1130 provided at the outer circumferential surface of the cover 1100 is not locked to the axial groove 1635. As described above, because the cover 1100 is non-rotatably connected by the shaft part 1761 of the base part 1760, the protruding part 1130 does not interfere with the rotation of the rotating operating part 1600 when the rotating operating part 1600 is rotated.

The prism part 1500 is formed of a transparent material and is disposed inside the outer circumferential cylindrical part 1610 at a side in front of the conical part 1620. The prism part 1500 has an axial direction hole 1530 having an axial center as a center. The cartridge assembly 1300 is disposed in the axial direction hole 1530. An axial groove 1510 connected to the axial groove 1635 of the inner circumferential cylindrical portion 1630 of the rotating operating part 1600 is provided in a portion of an inner circumferential surface of the axial direction hole 1530. The axial groove 1510 serves as a guide for passing the protruding part 1130 of the cover 1100 and the protruding part 1470 of the holding part 1400 therethrough when the cartridge assembly 1300 is detached from the aromatic device 1000. The prism part 1500 is fixed to the rotating operating part 1600 and rotates along with the rotation of the rotating operating part 1600. Likewise, the axial groove 1510 of the prism part 1500 prevents the protruding part 1130 provided at the outer circumferential surface of the cover 1100 from being locked when the rotating operating part 1600 is rotated.

The base part 1760 configured to support the cartridge assembly 1300 is held inside a cylindrical member 1851 directly or indirectly supported by the case body 1700. The rotating operating part 1600 is axially rotatably mounted at an end at a front side of the cylindrical member 1851. Also, one end side of the spring 1853 configured to bias the locking member 1855 toward the outer circumferential surface of the cartridge assembly 1300 is supported by the cylindrical member 1851.

The base part 1760 has the shaft part 1761 extending forward in the axial direction. The shaft part 1761 is inserted into the opening 1430 of the holding part 1400 and an axial direction hole 1220 of the perfume cartridge 1200. The rotation preventing part 1769 at the distal end of the shaft part 1761 is inserted into the accommodating part 1121 provided in the cover 1100.

Further, the base part 1760 has the supply port 1765 for air supplied from the air pump 1840. The air flow passages 1210 communicating with the supply port 1765 are switched by the perfume cartridge 1200 and the holding part 1400 being rotated relative to the base part 1760. In the example illustrated in FIG. 2, a distal end of a piston 1830 having a passage 1831 configured to guide air pumped by the air pump 1840 can advance and retract in the supply port 1765 of the base part 1760.

Specifically, the piston 1830 advances and retracts in the supply port 1765 by the spring 1815 biasing the base part 1760 toward the front side in the axial direction and the base part 1760 moving in the axial direction when the cartridge assembly 1300 is detached therefrom. A front side of the supply port 1765 is formed in a tapered shape having a diameter which gradually decreases in a forward direction. Because an outlet portion of the supply port 1765 is brought into proximity with the base part 1760, leakage of air is minimized.

The base part 1760 forms a part of a detaching mechanism configured to enable a user to easily detach the cartridge assembly 1300. The detaching mechanism will be described in detail below.

(3-2. Rotary Switching Mechanism)

Next, a rotary switching mechanism of the aromatic device 1000 according to the present embodiment will be described in detail with reference to FIGS. 25 to 32.

Figure 25:
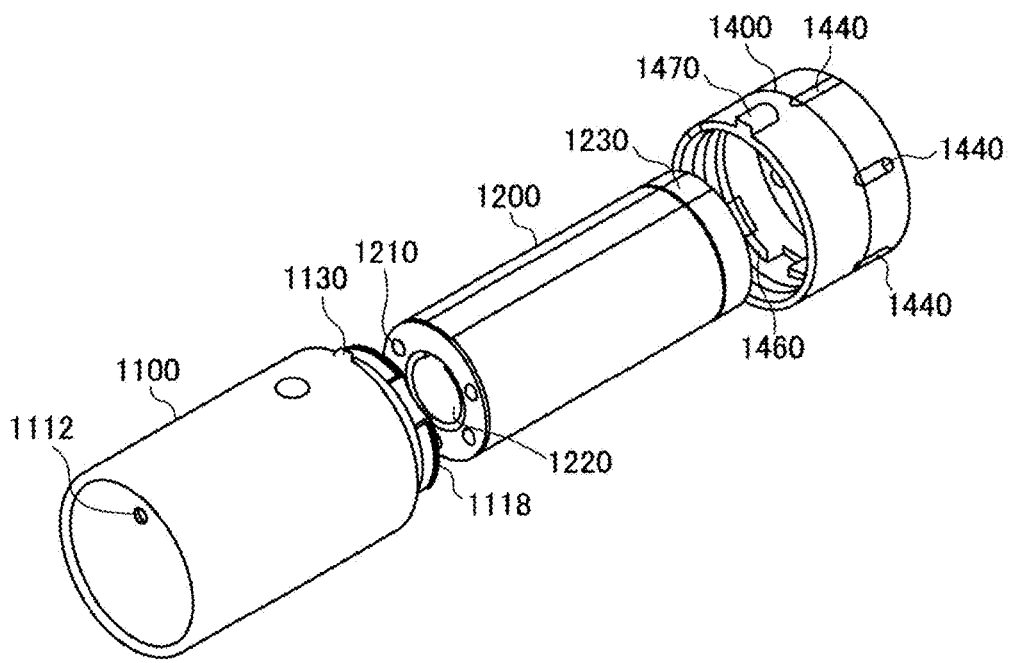
FIG. 25 is an exploded perspective view of a cartridge assembly of the aromatic device according to the same embodiment.
Figure 26:
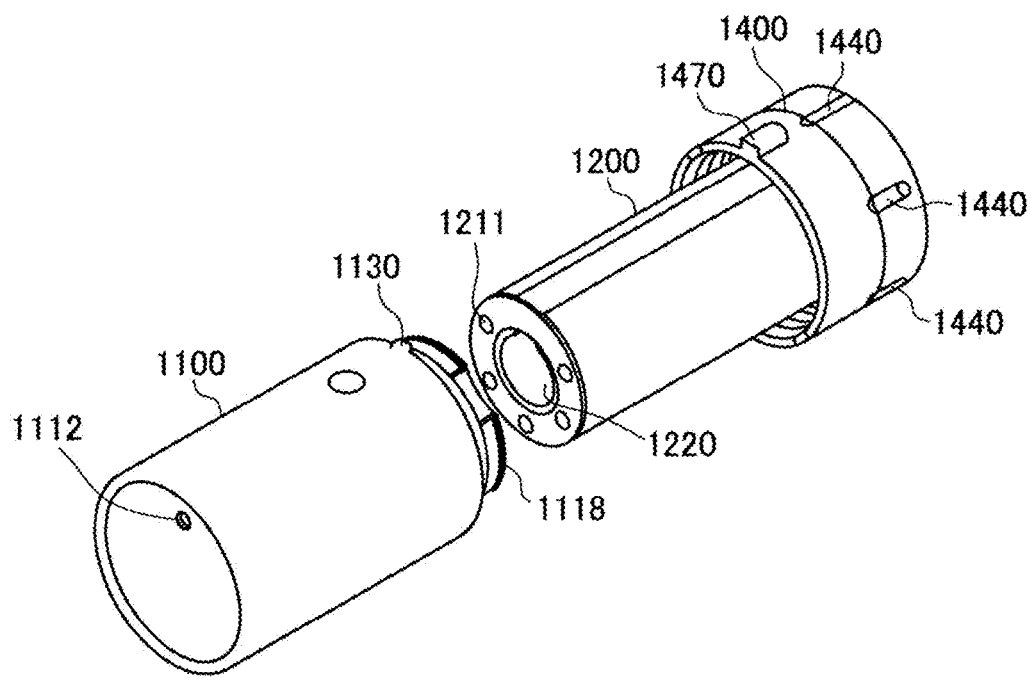
FIG. 26 is an explanatory diagram illustrating a state in which a perfume cartridge is fixed to a holding part.
Figure 27:
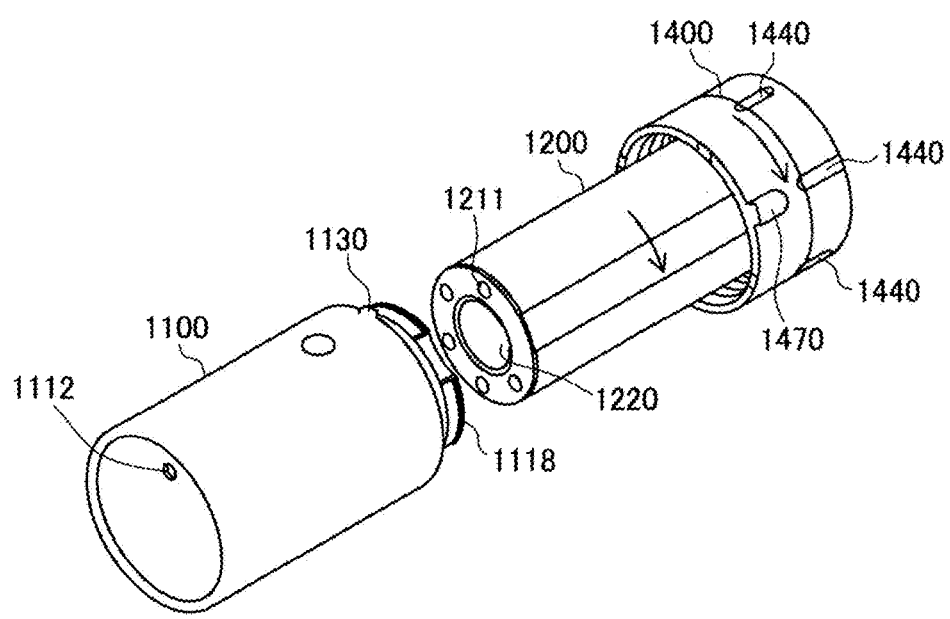
FIG. 27 is an explanatory diagram illustrating a state in which a perfume cartridge is rotated in synchronization with a holding part.

FIG. 25 is an exploded perspective view of the cartridge assembly 1300, FIG. 26 is an explanatory diagram illustrating a state in which the perfume cartridge 1200 is fixed to the holding part 400, and FIG. 27 is an explanatory diagram illustrating state in which the perfume cartridge 1200 rotates in synchronization with the holding part 400.

The perfume cartridge 1200 has a flat part 1230 for positioning at a portion of the outer circumferential surface of the rear end. A flat part (not illustrated) at which the flat part 1230 of the perfume cartridge 1200 is disposed is provided at a portion of the inner surface of the holding part 1400. Therefore, it may be impossible for the perfume cartridge 1200 to rotate relative to the holding part 1400. On one hand, a claw part 1118 configured to be engage with a claw part 1460 provided at an inner circumferential surface of the holding part 1400 is provided at the rear end of the cover 1100. The claw part 1460 of the holding part 1400 and the claw part 1118 of the cover 1100 connect the cover 1100 and the holding part 1400 to each other to be relatively rotatable. Therefore, as schematically illustrated in FIGS. 26 and 27, the perfume cartridge 1200 rotates in synchronization with the rotation of the holding part 1400 whereas the cover 1100 does not rotate.

Figure 28:
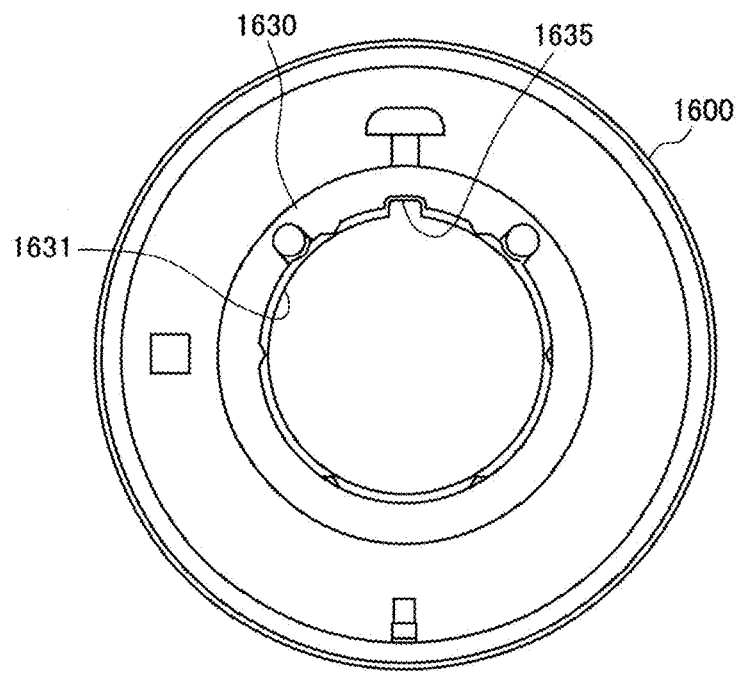
FIG. 28 is a view of a rotating operating part when seen from a rear side.
Figure 29:
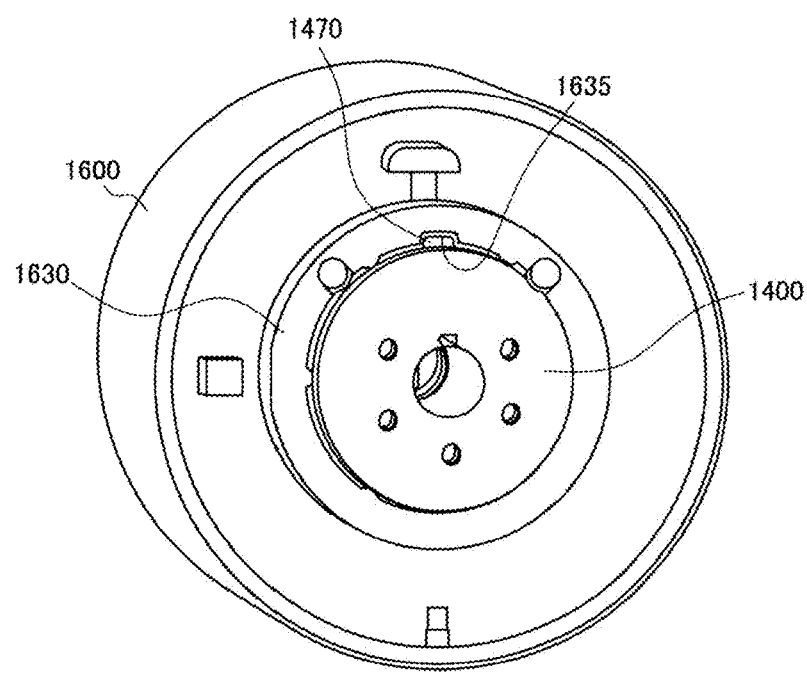
FIG. 29 is a view of a rotating operating part having a cartridge assembly mounted thereon when seen from a rear side.

FIG. 28 is a view of the rotating operating part 1600 when seen from the rear side, and FIG. 29 is a view of the rotating operating part 1600 having the cartridge assembly 1300 mounted thereon when viewed from the rear side.

The axial groove 1635 is provided in a portion of the inner circumferential surface 1631 of the inner circumferential cylindrical part 1630 of the rotating operating part 1600. In the cartridge assembly 1300 having the perfume cartridge 1200 accommodated therein and configured to connect the cover 1100 and the holding part 1400 to each other, the protruding part 1470 provided at the outer circumferential surface of the holding part 1400 is engaged with the axial groove 1635 of the rotating operating part 1600, and rotations of the rotating operating part 1600 and the holding part 1400 are synchronized with each other. As described above, because the rotations of the holding part 1400 and the perfume cartridge 1200 are synchronized with each other, the perfume cartridge 1200 can be ultimately rotated by the rotating operating part 1600 being rotated.

Further, in a state in which the perfume cartridge 1200 and the holding part 1400 are aligned with each other, the protruding part 1470 of the holding part 1400 and the protruding part 1130 of the cover 1100 are aligned with each other, and the cartridge assembly 1300 is assembled, none of the air flow passages 1210 of the perfume cartridge 1200 communicate with the scent releasing port 1112. Therefore, when the perfume cartridge 1200 is carried or replaced or the aromatic device 1000 is not in use, the air flow passages 1210 are not open to the outside, and the perfume cartridge 1200 can last longer.

Figure 30:
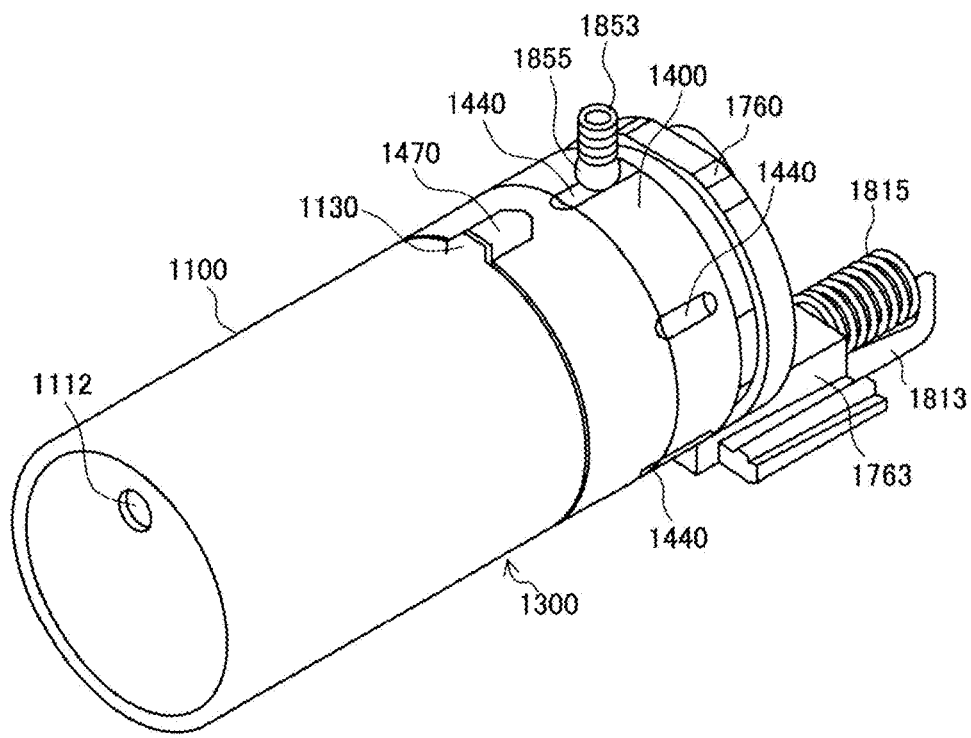
FIG. 30 is a perspective view illustrating a cartridge assembly supported by a base part.
Figure 31:
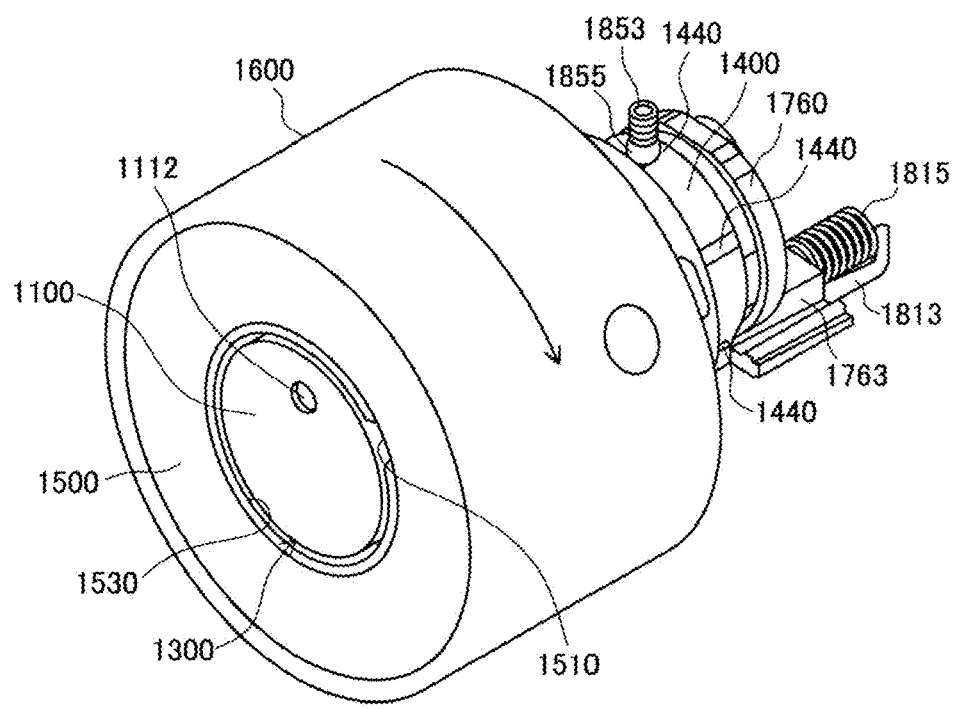
FIG. 31 is an explanatory diagram illustrating an operation when a rotating operating part is rotated.

FIG. 30 is a perspective view illustrating a state in which the cartridge assembly 1300 is supported by the base part 1760. When the cartridge assembly 1300 is inserted into the axial direction hole 1530 of the prism part 1500 fixed to the rotating operating part 1600 and is supported by the base part 1760, the locking member 1855 enters one of the groove parts 1440. From this state, when the rotating operating part 1600 is rotated 60° as illustrated in FIG. 31, the holding part 1400 and the perfume cartridge 1200 rotate in synchronization therewith and the cover 1100 and the base part 1760 do not rotate.

Figure 32:
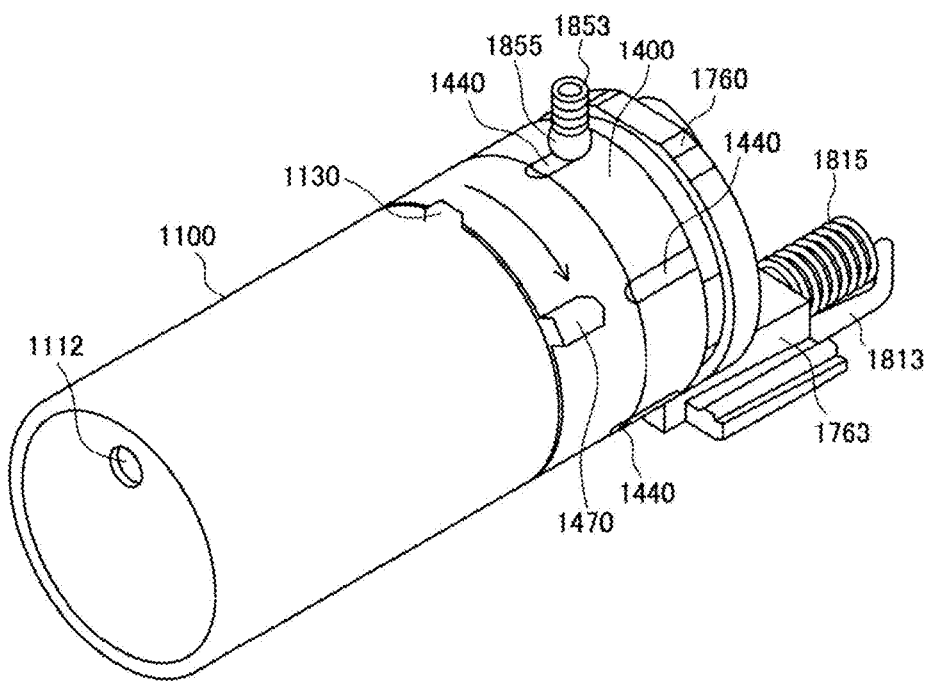
FIG. 32 is an explanatory diagram illustrating an operation of a cartridge assembly when a rotating operating part is rotated.

As a result, as illustrated in FIG. 32, the locking member 1855 slides along a circumferential surface of the holding part 1400 and then enters the next groove part 1440. In this state, a rear end side opening of a single air flow passage 1210 communicates with the supply port 1765 for air supplied from the air pump 1840, and a distal end side opening communicates with the scent releasing port 1112 of the cover 1100. In this way, air passes through the air flow passage 1210 and a scent is released when the air pump 1840 is driven.

(3-3. Detaching Mechanism)

Next, the detaching mechanism configured to facilitate detaching the cartridge assembly 1300 will be described in detail. The aromatic device 1000 according to the present embodiment includes a detaching mechanism using a heart cam mechanism.

Figure 33:
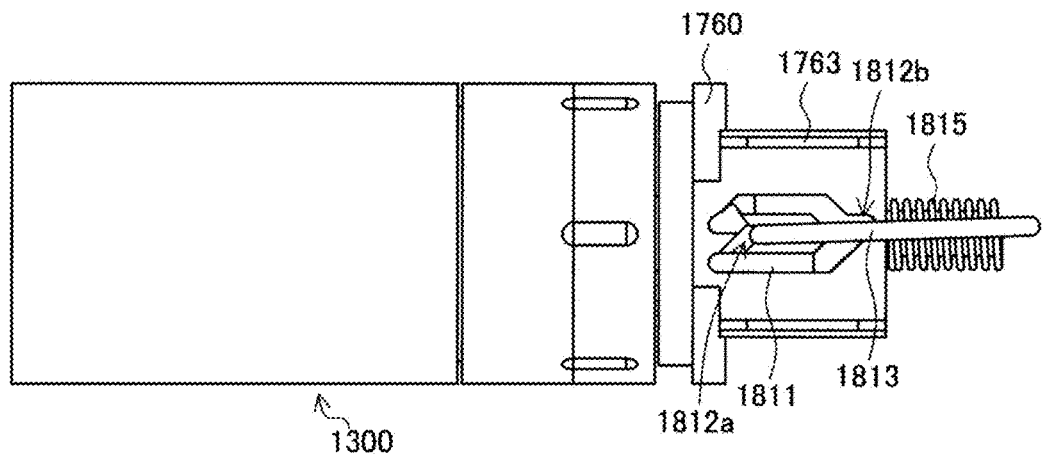
FIG. 33 is a side view illustrating a detaching mechanism of the cartridge assembly of the aromatic device according to the same embodiment.

FIG. 33 is a view of the cartridge assembly 1300 supported by the base part 1760 when seen in a diametric direction thereof (corresponding to a view in which the cartridge assembly 1300 and the base part 1760 indicated in the cross-section of FIG. 23 are viewed from a lower side). The heart cam mechanism has a cam part 1763, an engaging pin 1813 which is an elastic member, and the spring 1815 configured to bias the cam part 1763 toward the front side. The cam part 1763 is erected along the axial direction from a portion of an edge portion of the base part 1760 toward the rear side. The cam part 1763 has a substantially rectangular parallelepiped outer shape, and a cam groove 1811 is provided at a surface which faces outward in a diametric direction of the base part 1760.

The engaging pin 1813 has a substantially U shape, and one end thereof is disposed in the cam groove 1811. The other end of the engaging pin 1813 is fixed at an appropriate position in the case body 1700, and one end of the engaging pin 1813 is biased toward the cam part 1763. The cam groove 1811 has a plurality of stepped surfaces in the groove, and the one end of the engaging pin 1813 may be located at a first position 1812a or a second position 1812b.

FIGS. 23 and 33 illustrate a state in which the cartridge assembly 1300 is mounted in the aromatic device 1000. Here, the cam part 1763 is biased toward the front side by the spring 1815, and the one end of the engaging pin 1813 is locked at the first position 1812a.

Figure 34:
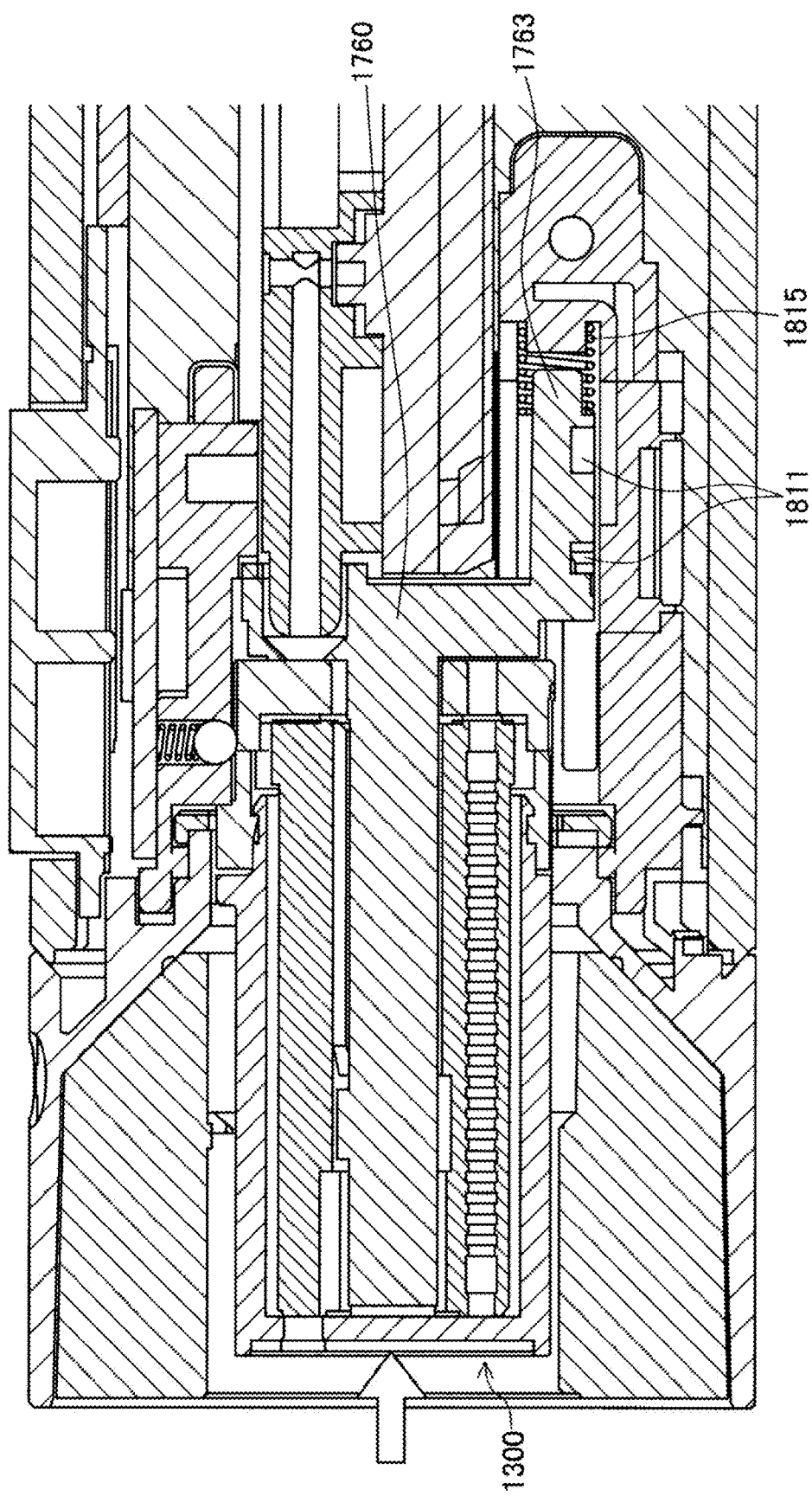
FIG. 34 is an axial cross-sectional view of an aromatic device for describing an operation of a detaching mechanism.
Figure 35:
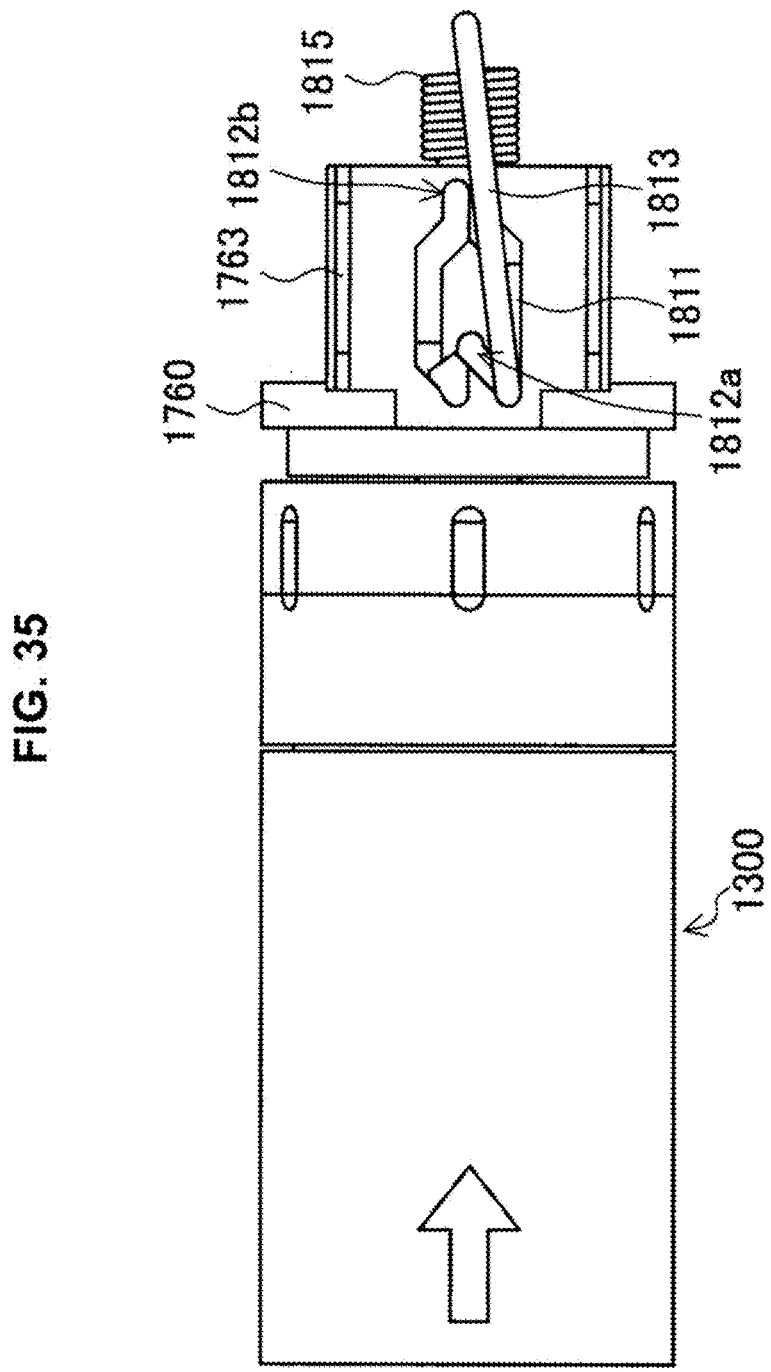
FIG. 35 is an explanatory diagram illustrating an operation of a detaching mechanism.

FIGS. 34 and 35 illustrate an operation of a detaching mechanism when the cartridge assembly 1300 is detached from the aromatic device 1000. In this case, the cartridge assembly 1300 is pushed toward the rear side (the right side in the figure) by a user. The spring 1815 is compressed, and the cam part 1763 moves toward the right side. Here, the one end of the engaging pin 1813 moves toward the lower side of the cam groove 1811 illustrated in FIG. 35 by a step on a bottom surface of the cam groove 1811. From this state, when the user releases the pushed-in cartridge assembly 1300, the cam part 1763 is moved toward the front side (the left side in the figure) by the spring 1815. Accordingly, the one end of the engaging pin 1813 moves within a groove at the lower side of the cam groove 1811 illustrated in FIG. 35 due to the step on the bottom surface of the cam groove 1811.

Figure 36:
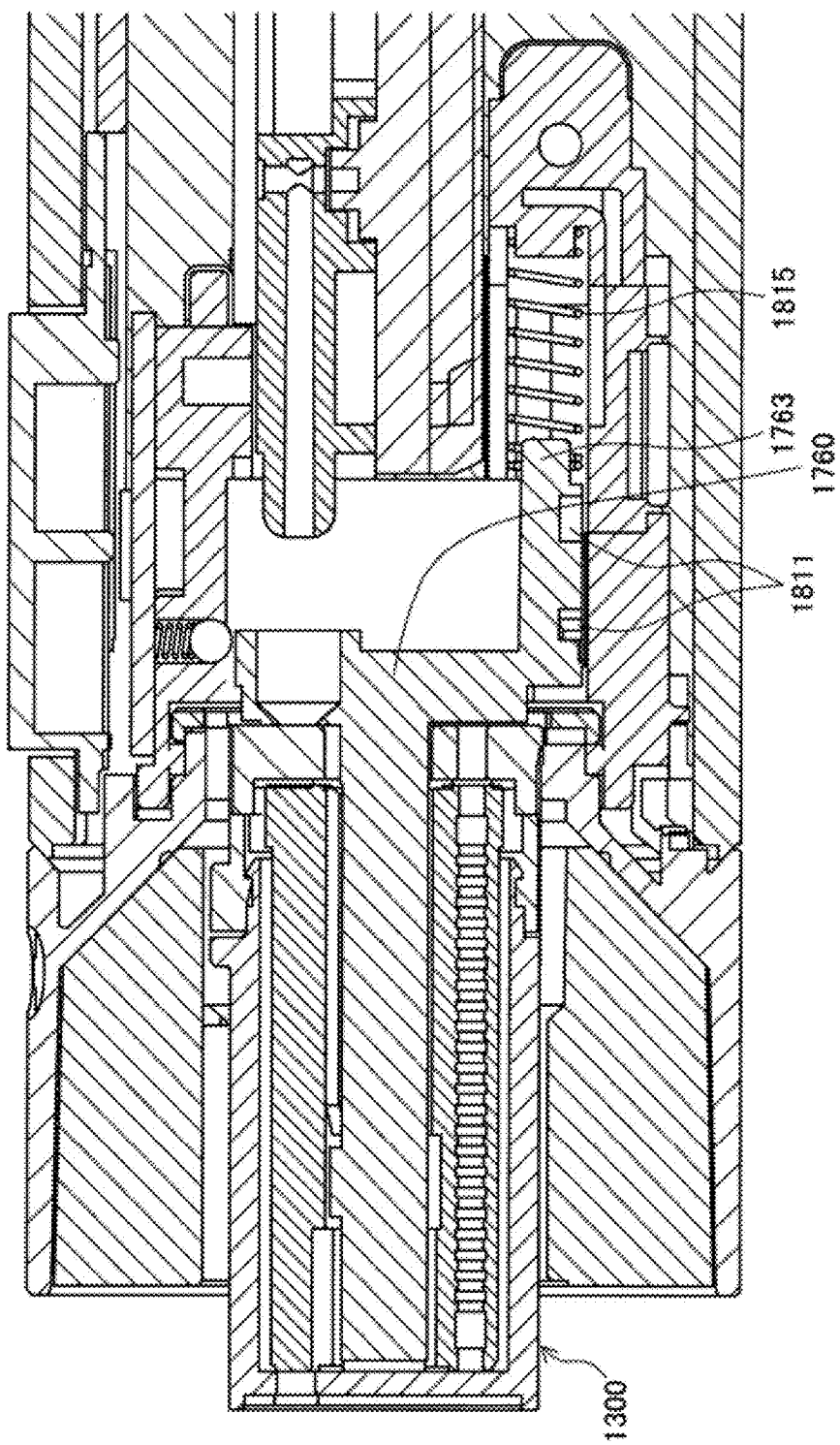
FIG. 36 is an axial cross-sectional view of an aromatic device for describing an operation of a detaching mechanism.
Figure 37:
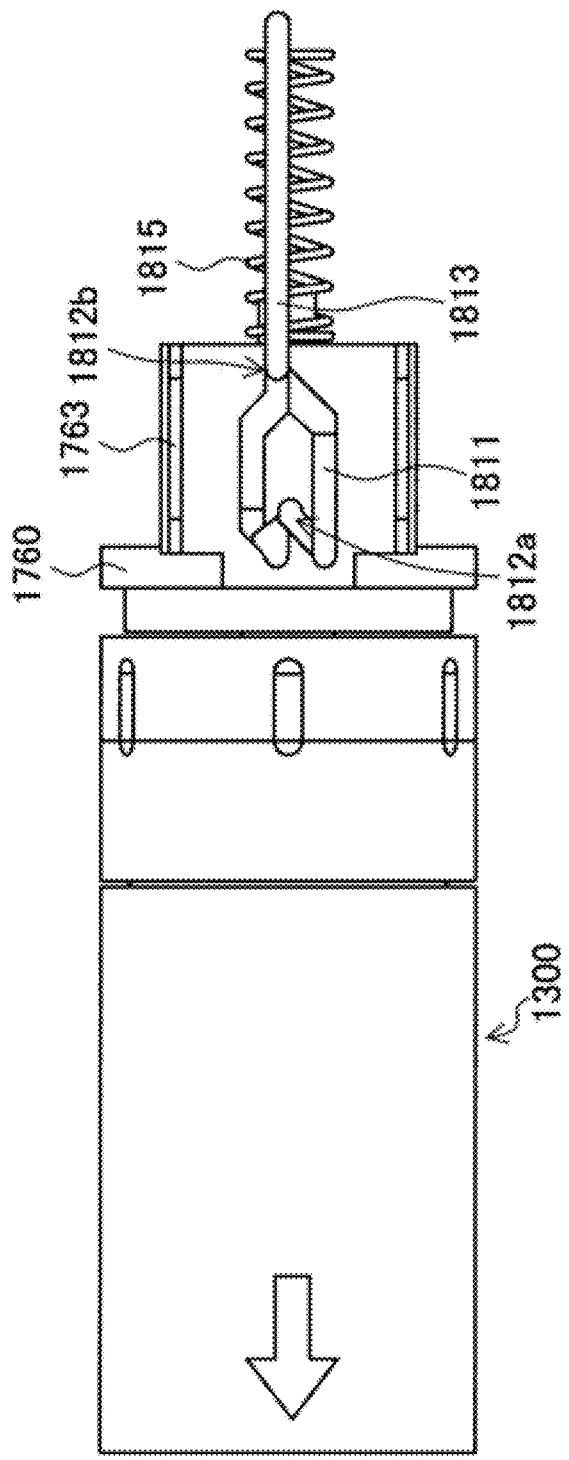
FIG. 37 is an explanatory diagram illustrating an operation of a detaching mechanism.

FIGS. 36 and 37 illustrate a state in which the cartridge assembly 1300 is detachable from the aromatic device 1000. The cam part 1763 is biased toward the front side by the spring 1815, and the one end of the engaging pin 1813 is locked at the second position 1812b. In this state, one end an end at the front side of the cartridge assembly 1300 protrudes from the prism part 1500 fixed to the rotating operating part 1600. Therefore, because the user can hold the end at the front side of the cartridge assembly 1300, the cartridge assembly 1300 is detachable.

When the cartridge assembly 1300 is mounted and the cartridge assembly 1300 is pushed toward the rear side (the right side in the figure) from the state illustrated in FIGS. 36 and 37, the cam part 1763 moves toward the rear side. In this case, the one end of the engaging pin 1813 moves within a groove at an upper side of the cam groove 1811 illustrated in FIG. 37 due to the step on the bottom surface of the cam groove 1811. In this way, as illustrated in FIGS. 23 and 33, the one end of the engaging pin 1813 is locked at the first position 1812a.

As described above, the aromatic device 1000 according to the present embodiment includes a detaching mechanism configured to facilitate detaching the cartridge assembly 1300. Therefore, even with a small aromatic device 1000 such as a portable aromatic device 1000, a user can easily replace the cartridge assembly 1300.

The configuration of the aromatic device 1000 according to the present embodiment other than the points described above may be configured identically to the aromatic device according to the first embodiment or the second embodiment.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, although the cartridge case 300 and the perfume cartridge 200 are rotated by the rotating operating part 600 being rotated to change the air flow passages 211, 213, 215, 217, and 219 through which air passes in the above embodiment, the present disclosure is not limited to such an example. For example, a rotatable member having a flow passage may be provided between the air supply port 750 and the holding part 400, and the air flow passages 211, 213, 215, 217, and 219 communicating with the air supply port 750 may be switched by the member being rotated. Alternatively, the air flow passages 211, 213, 215, 217, and 219 to be opened may be switched by using a mask, a cap, or the like configured to open and close the air flow passages 211, 213, 215, 217, and 219 and rotating the mask or the like.

In such a configuration example, a member (corresponding to the first member) configured to integrally rotate with the rotatable member having the flow passage or along with the rotation of the mask or the cap and configured to rotate relative to the perfume cartridge 200 may be disposed in the mirror surface part 622. Further, in such a configuration example, an indicating part configured to indicate a selection target may be disposed at a rotation position of the rotatable member having the flow passage or the mask or the cap. The indicating part may be, for example, a marking display. Also, in the configuration example, the perfume cartridge 200 or the base part 700 corresponds to the second member.

Further, although the scent releasing port 122 serves as the indicating part configured to indicate the selected air flow passages 211, 213, 215, 217 and 219 in the above embodiment, the present disclosure is not limited to such an example. The indicating part may be anything that may be a mark, such as a protrusion or a marking display, capable of being visually recognized from the axial direction of the first member (the cartridge case in the above example).

Further, although the cartridge case 300 configured to hold the perfume cartridge 200 therein and integrally rotate with the perfume cartridge 200 corresponds to the first member in the above embodiment, the cartridge case may not be included, and the perfume cartridge 200 may be the first member. In this case, predetermined information is displayed on the outer circumferential surface of the perfume cartridge 200.

Further, although the air flow passages 211, 213, 215, 217, and 219 provided in the perfume cartridge 200 are disposed at equal intervals on a circumference of a single circle in the above embodiment, the present disclosure is not limited to such an example. For example, a plurality of air flow passages may be disposed at equal intervals on each of two or more concentric circles having an axial center of the perfume cartridge 200 as a center. In this case, a mechanism configured to change a supply destination of air supplied from the air supply port 750 in the diametric direction of the perfume cartridge 200 may be provided at any position between the air supply port 750 and the perfume cartridge 200. Here, the third cylindrical member (fourth member) 930 provided in the rotary switching device according to the second embodiment may move in the axial direction along with the switching of the supply destination of air in the diametric direction. In this way, when the rotary switching device is viewed in the axial direction, information displayed on the third cylindrical member (the fourth member) 930 may be superimposed to be displayed on information displayed on the outer circumferential surface of the first cylindrical member 910 (the cartridge case 300), and a desired air flow passage may be easily selected among the plurality of air flow passages disposed on each of the concentric circles.

Further, although not illustrated, to keep the air flow passages 211, 213, 215, 217, and 219 closed when not in use, the aromatic device 1 may include a suitable valve device, a shutter device, a seal device, and any other closing device.

Further, although the aromatic device 1 is described as an example of the rotary switching device in the above embodiment, the rotary switching device of the present disclosure is not limited to such an example. For example, selection elements may be music files, and the rotary switching device may be applied to an audio playback device in which music being played is switched depending on relative positions of a first member and a second member which may rotate relative to each other. Alternatively, selection elements may be wicks of a ballpoint pen, and the rotary switching device may be applied to a writing tool in which colors of the ballpoint pen are switched depending on relative positions of a first member and a second member which may rotate relative to each other. Regardless of objects to which the rotary switching device is applied, a user may easily change a selected target while viewing the rotary switching device from the axial direction.

Additionally, the present technology may also be configured as below.

(1)

A rotary switching device including:

a cylindrical first member that includes an outer circumferential surface on which predetermined information is displayed;

a second member that is rotatable relative to the first member;

a plurality of selection elements among which a selection target is switched in accordance with relative positions of the first member and the second member;

a mirror surface part that is formed by a surface disposed around the outer circumferential surface of the first member and intersecting an axial direction of the first member, and that is configured to specularly reflect the information displayed on the outer circumferential surface of the first member to enable the information to be visually recognized from the axial direction of the first member; and an indicating part configured to indicate the selection element that is selected.

(2)

The rotary switching device according to (1), in which the information displayed on the first member is information for identifying each of the selection elements.

(3)

The rotary switching device according to (1) or (2), including a cylindrical third member that is formed by transparent material, disposed between the first member and the mirror surface part, and rotatable relative to at least the first member.

(4)

The rotary switching device according to (3), in which the information displayed on the outer circumferential surface of the first member is superimposed on information displayed on the third member and is visually recognized from the axial direction of the first member.

(5)

The rotary switching device according to any one of (1) to (4), including a fourth member that is formed by transparent material, disposed between the first member and the mirror surface part, and that has a position adjustable along the axial direction of the first member.

(6)

The rotary switching device according to (5), in which the information displayed on the outer circumferential surface of the first member is superimposed on information displayed on the fourth member and is visually recognized from the axial direction of the first member.

(7)

The rotary switching device according to any one of (1) to (6) including a rotating operating part that is disposed outside the mirror surface part, in which the first member or the second member is rotated by rotating the rotating operating part.

(8)

The rotary switching device according to any one of (1) to (7), in which the mirror surface part is formed with a conical or pyramid surface.

(9)

The rotary switching device according to any one of (1) to (8), including a prism part that is formed by transparent material, disposed between the first member and the mirror surface part, and that has an axial direction hole in which the first member is disposed.

(10)

The rotary switching device according to any one of (1) to (9), in which the plurality of selection elements are replaceable.

(11)

The rotary switching device according to (1) to (10), including:

a main body part;

a plurality of air flow passages each of which has both ends that are open and each of which is disposed on a circumference centered on an axial center; and perfume that is held in at least a portion of an inner surface of the air flow passages, in which a perfume cartridge that is axially rotatable along with the first member is held in the first member; and the selection elements are the plurality of air flow passages.

(12)

The rotary switching device according to (11), in which the second member has a supply port for air blown from a blower; and the air flow passages communicating with the supply port are switched by relative rotation between the first member and the second member.

(13)

The rotary switching device according to (12), including a cylindrical third member that is formed by transparent material, disposed between the first member and the mirror surface part, and rotatable relative to at least the first member, in which the first member has a plurality of holes each of which is configured to communicate with an opening at another end side communicating with the supply port among openings at both ends of the plurality of air flow passages; and the third member has a scent releasing port that serves as the indicating part and that is configured to communicate with air flow passages communicating with the supply port.

(14)

An aromatic device including:

a perfume holding member provided with a plurality of air flow passages passing therethrough and configured to hold a perfume, a member having a supply port configured to communicate with some of the air flow passages of the plurality of air flow passages and introduce air supplied from a wind power source to some of the air flow passages, and a rotary switching mechanism configured to relatively rotate the perfume holding member so that some of the air flow passages communicating with the supply port are switched.

REFERENCE SIGNS LIST

1 aromatic device
100 cover (third member)
112 scent releasing port (indicating part)
200 perfume cartridge
211, 213, 215, 217, 219 air flow passage (selection element)
300 cartridge case (first member)
400 holding part
500 prism part
600 rotating operating part
620 conical part
622 mirror surface part
700 base part (second member)
750 air supply port
910 first cylindrical member
920 second cylindrical member
930 third cylindrical member

The invention claimed is:

1. A rotary switching device comprising:
a cylindrical first member that includes an outer circumferential surface on which predetermined information is displayed;
a second member that is rotatable relative to the first member;
a plurality of selection elements among which a selection target is switched in accordance with relative positions of the first member and the second member;
a mirror surface part that is formed by a surface disposed around the outer circumferential surface of the first member and intersecting an axial direction of the first member, and that is configured to specularly reflect the information displayed on the outer circumferential surface of the first member to enable the information to be visually recognized from the axial direction of the first member; and
an indicating part configured to indicate the selection element that is selected.

2. The rotary switching device according to claim 1, wherein the information displayed on the first member is information for identifying each of the selection elements.

3. The rotary switching device according to claim 1, comprising
a rotating operating part that is disposed outside the mirror surface part, wherein
the first member or the second member is rotated by rotating the rotating operating part.

4. The rotary switching device according to claim 1, wherein the mirror surface part is formed with a conical or pyramid surface.

5. The rotary switching device according to claim 1, comprising
a prism part that is formed by transparent material, disposed between the first member and the mirror surface part, and that has an axial direction hole in which the first member is disposed.

6. The rotary switching device according to claim 1, wherein the plurality of selection elements are replaceable.

7. The rotary switching device according to claim 1, comprising
a cylindrical third member that is formed by transparent material, disposed between the first member and the mirror surface part, and rotatable relative to at least the first member.

8. The rotary switching device according to claim 7, wherein the information displayed on the outer circumferential surface of the first member is superimposed on information displayed on the third member and is visually recognized from the axial direction of the first member.

9. The rotary switching device according to claim 1, comprising
a fourth member that is formed by transparent material, disposed between the first member and the mirror surface part, and that has a position adjustable along the axial direction of the first member.

10. The rotary switching device according to claim 9, wherein the information displayed on the outer circumferential surface of the first member is superimposed on information displayed on the fourth member and is visually recognized from the axial direction of the first member.

11. The rotary switching device according to claim 1, comprising:
   a main body part;
   a plurality of air flow passages each of which has both ends that are open and each of which is disposed on a circumference centered on an axial center; and
   perfume that is held in at least a portion of an inner surface of the air flow passages, wherein
   a perfume cartridge that is axially rotatable along with the first member is held in the first member; and
   the selection elements are the plurality of air flow passages.

12. The rotary switching device according to claim 11, wherein
   the second member has a supply port for air blown from a blower; and
   the air flow passages communicating with the supply port are switched by relative rotation between the first member and the second member.

13. The rotary switching device according to claim 12, comprising
   a cylindrical third member that is formed by transparent material, disposed between the first member and the mirror surface part, and rotatable relative to at least the first member, wherein
   the first member has a plurality of holes each of which is configured to communicate with an opening at another end side communicating with the supply port among openings at both ends of the plurality of air flow passages; and
   the third member has a scent releasing port that serves as the indicating part and that is configured to communicate with air flow passages communicating with the supply port.

* * * * *